US006627195B1

(12) United States Patent
Paul

(10) Patent No.: US 6,627,195 B1
(45) Date of Patent: Sep. 30, 2003

(54) BINDING AGENTS TO CD23

(75) Inventor: Jean-Yves Marcel Paul, Geneva (CH)

(73) Assignee: Smithkline Beecham Corporation, Philadelphia, PA (US)

( * ) Notice: Subject to any disclaimer, the term of this patent is extended or adjusted under 35 U.S.C. 154(b) by 809 days.

(21) Appl. No.: 08/817,719

(22) PCT Filed: Oct. 20, 1995

(86) PCT No.: PCT/EP95/04109

§ 371 (c)(1),
(2), (4) Date: Jul. 11, 1997

(87) PCT Pub. No.: WO96/12741

PCT Pub. Date: May 2, 1999

(30) Foreign Application Priority Data

Oct. 25, 1994 (GB) .............................................. 9421463
Jun. 20, 1995 (GB) .............................................. 9512480
Jun. 30, 1995 (GB) .............................................. 9513415

(51) Int. Cl.$^7$ ........................ A61K 38/00; A61K 39/00

(52) U.S. Cl. ................................ 424/133.1; 424/135.1; 424/144.1; 424/145.1; 424/153.1; 424/154.1; 424/158.1; 514/2

(58) Field of Search ........................ 424/144.1, 154.1, 424/158.1, 133.1, 192.1, 198.1, 135.1, 153.1, 145.1; 514/2

(56) References Cited

U.S. PATENT DOCUMENTS 5,530,101 A * 6/1996 Queen et al.

OTHER PUBLICATIONS

Hawkins et al. Brit. S. Med. 305: 1349, 1992.*
Hellen et al. J.Clin. Pathol. 44: 293–296, 1991.*
Bonnefog et al. Immunology Today 14:1–2, 1993.*
Bansai et al. Clin Exp. Rheumatology.*
Flores–Ramo et al. Science 261: 1038, 1993.*
Queen et al PNAS 86:10029, 1989.*
Reiter et al. Anthritis and Rheumatism 34: 525, 1991.*
Burmesten et al. Clin. Exp. Rheumatology 11:5139–5145, 1993.*
Bonnefoy et al, "Inhibition of human interleukin 4–induced IgE synthesis by a subset of anti–CD23/FcεRII monoclonal antibodies", Eur. J. Immunol. 20:139–144 (1990).
Bacon et al, "CD21 expressed on basophilic cells is involved in histamine release triggered by CD23 and anti–CD21 antibodies", Eur. J. Immunol. 23:2721–2724 (1993).
Yu et al, "Negative feedback regulation of IgE synthesis by murine CD23", Nature 369:753–759 (1994).
Williams et al, "Regulation of Low Affinity IgE Receptor (CD23) Expression on Mononuclear Phagocytes in Normal and Asthmatic Subjects", The Journal of Immunology 149(8):2823–2829 (1992).

Armant et al, "Regulation of Cytokine Production by Soluble CD23: Costimulation of Interferon γ Secretion and Triggering of Tumor Necrosis Factor α Release", J. Exp. Med. 180:1005–1011 (1994).
Al–Janadi et al. "Soluble CD23 and Interleukin–4 Levels in Autoimmune Chronic Active Hepatitis and Systemic Lupus Erythematosus" Clin. Immunol. Pathol. 71:33–37 (1994).
Aubry et al. "CD23 Interacts with a New Functional Extra-cytoplasmic Domain Involving N–Linked Oligosaccharides on CD21" J. Immunol. 152:5806–5813 (1994).
Aubry, et al. "CD21 is a Ligand for CD23 and Regulates IgE Production" Nature 358:505–507 (1992).
Bach "Immunosuppressive Therapy of Autoimmune Diseases" 14:322–326 (1993).
Bansal et al. "Variations in Serum sCD23 in Conditions with Either Enhanced Humoral or Cell–Mediated Immunity" Immunol. 79:285–289 (1993).
Burastero et al. "Rheumatoid Arthritis with Monoclonal IgE Rheumatoid Factor" J. Rheumatol. 20:489–494 (1993).
Cho et al. "Studies on the Role of Interleukin–4 and Fc ε RII in the Pathogenesis of Minimal Change Nephrotic Syndrome" 7:343–348 (1992).
Delespesse et al. "Expression, Structure, and Function of the CD23 Antigen" Adv. Immunol. 49:149–491 (1991).
Dugas et al. "Triggering of CD23b Antigen by Anti–CD23 Monoclonal Antibodies Induces Interleukin–10 Production by Human Macrophages" Eur. J. Immunol. 26:1394–1398 (1996).
Fournier et al. "CD23 Antigen Regulation and Signaling in Chronic Lymphocytic Leukemia" J. Clin. Invest. 89:1312–1321 (1992).
Frémeaux–Bacchi et al. "Functional Properties of Soluble CD21" Immunopharmacology 42:31–37 (1999).
Frémeaux–Bacchi et al. "Soluble CD21 Induces Activation and Differentiation of Human Monocytes Through Binding to Membrane CD23" Eur. J. Immunol. 28:4268–4274 (1998).
Gordon "B–cell Signalling via the C–Type Lectins CD23 and CD72" Immunology Today 15:411–417 (1994).
Gordon et al. "CD23: a Multi–Functional Recetor/Lymphokine?" Immunology Today 10:153–157 (1989).
Guy et al. "Coordinated Action of IgE and a B–cell–stimulatory Factor on the CD23 Receptor Molecule Up–regualtes B–lymphocyte Growth" Proc. Natl. Acad. Sci. 84:6239–6243 (1987).
Ikizawa et al. "Possible Role CD5 B Cells Expressing CD23 in Mediating the Elevation of Serum–Soluble CD23 in Patients with Rheumatoid Arthritis" Int. Arch. Allergy Immunol. 101:416–424 (1993).

(List continued on next page.)

*Primary Examiner*—David Saunders
(74) *Attorney, Agent, or Firm*—Nixon & Vanderhye P.C.

(57) ABSTRACT

The present invention relates to agents that bind CD23 and that can be used in the treatment of inflammatory, autoimmune or allergic diseases.

13 Claims, 12 Drawing Sheets

OTHER PUBLICATIONS

Itoh et al. "Surface Expression and Release of Soluble forms of CD8 and CD23 in CD40–and IL–4–activated Mononuclear Cells form Patients with Graves' Disease (GD)" Clin. Exp. Immunol. 113:309–314 (1998).

Kolb et al. "Ligation of CD23 Triggers Cyclic AMP Generation in Human B Lymphocytes" J. Immunol. 150:4798–4809 (1993).

Bansel "Soluble CD23 Levles are Elevated in the Serum of Patients with Primary Sjögren's Syndrome and Systemic Lupus Erythematosus" Clin. Exp. Immnol. 89:452–455 (1992).

Kumagai et al. "Possible Different Mechanisms of B Cell Activation in Systemic Lupus Erythematosus and Rheumatoid Arthritis: Opposite Expression of Low–Affinity Receptors for IgE (CD23) on Their Peripheral B Cells" Exp. Immunol. 78:348–353 (1989).

Morris et al. "Induction of B Cell and T Cell Tolerance in Vivo by Anti–CD23 mAB" J. of Immunol. 152:3768–3776 (1994).

Müller et al. "Mononuclear Cell–bound CD23 is Elevated in Both Atopic Dermatitis and Psoriasis" J. of Dermatological Science 2:125–133 (1991).

Nakamura et al. "In Vitro IgE Inhibition in B Cells by Anti–CD23 Monoclonal Antibodies is Functionally Dependent on the Immunoglublin Fc Domain" Immunopharmacol 22:131–141 (2000).

Saxon et al. "Inhibition of Human IgE Production Via FceR–II Stimulation Results from a Decrease in the mRNA for Secreted but not Membrane $\epsilon$ H Chains" J. Immunol. 147:4000–4006 (1991).

Schad "T Cell Tolerance: Models for Clinical Application to Allergy and Autoimmunity" Chem. Immunol. 58:193–205 (1994).

Senju et al. "Two–Color Immunofluorescence and Flow Cytometric Analysis of Lamina Propria Lymphocyte Subsets in Ulcerative Colitis and Crohn's Disease" Digestive Diseases and Sciences 36: 1453–1458 (1990).

Swendeman et al. "The Activation Antigen BLAST–2, When Shed, is an Autocrine BCGF for Normal and Transformed B Cells" EMBO J. 6:1637–1642 (1987).

Van der Harst et al. "Clonal B–Cell Populations in Patients with Idiopathic Thrombocytopenic Purpura" Blood 76:2321–2326 (1990).

Yano et al. "Increase of CD23–Positive Cells in Peripheral Blood from Ptients with IgA Nephropathy and Non–IgA Proliferative Glomerulonephritis" Nephron 60:404–410 (1992).

Yodoi et al., "Low Affinity of IgE Receptors: Regulation and Functional Roles in Cell Activation" John Wiley & Sons, Ciba Foundation Symposium 147 pp. 133–152 (1989).

Yoshikawa et al. "Soluble FceRII/CD23 in Patients with Autoimmune Diseases and Epstein–Barr Virus–Related Disorders: Analysis by ELISA for Soluble FceRII/CD23" Immunomethods 4:65–71 (1994).

Winter et al. "Humanized Antibodies" Immunology 14:243–246 (1993).

Three pages from Arthritis Foundation web site *www.arthritis.org/conditions/diseasecenter* (2001).

Notice of Opposition filed Oct. 22, 2001.

Reply to the Notice of Opposition filed May 2, 2002.

Summons to Attend Oral Proceedings and EPO Form 2906 (preliminary opinion) dated Aug. 20, 2002.

Henchez et al. "Stimulation of Human IgE Production by a Subset of Anti–CD21 Monoclonal Antibodies: Requirement of a Co–signal to Modulate $\epsilon$Transcripts" Immunol. 81:285–290 (1994).

* cited by examiner

BINDING AGENTS TO CD23

This is a 371 of PCT Application No. PCT/EP95/04109, filed Oct. 20, 1995.

The present invention relates to particular binding agents which can be used in the treatment of inflammatory, autoimmune or allergic diseases.

CD23 (FCεRII) is a type II molecule of the C-lectin family which also includes the lymphocyte homing receptor (MEL-14) and the endothelial leukocyte adhesion molecule-1 (ELAM 1). It is a low affinity receptor for IgE. In humans a variety of haematopoietic cell types express CD23 on their surface, including follicular dendritic cells, B cells, T cells and macrophages. CD23 molecules are also found in soluble forms in biological fluids. Soluble CD23 (sCD23) molecules are formed by proteolytic cleavage of transmembrane receptors. CD23 has pleiotropic activities including mediation of cell adhesion, regulation of IgE and histamine release, rescue of B cells from apoptosis and regulation of myeloid cell growth. These functional activities are mediated through the binding to specific ligands of cell-associated CD23, or sCD23, the latter acting in a cytokine-like manner (Conrad, D. H., *Annu Rev Immunol* 8, 623–645 1990); Delespesse, G., et al., *Adv Immunol* 49, 149–191 (1991); Bonnefoy, J. Y., et al., *Curr Opin Immunol* 5,944–947 (1993)).

Increased expression of CD23 has been observed in a number of inflammatory diseases. CD23 has been identified in synovial biopsies from patients with chronic synovitis, and sCD23 can be measured at concentrations exceeding the normal range in the serum and synovial fluid of patients with rheumatoid arthritis (Bansal, A. S., Oliver, W., Marsh, M. N., Pumphrey, R. S., and Wilson, P. B., *Immunology* 79, 285289 (1993); Hellen, E. A., Rowlands, D. C., Hansel, T. T., Kitas, G. D., and Crocker, J. J., *Clin Pathol* 44, 293–296 (1991); Chomarat, P., Brioloay, J., Banchereau, J., & Miossec, P., *Arthritis Rheum* 86, 234–242 (1993); Bansal, A., et al, *Clin Exp Immunol* 89, 452–455 (1992); Rezonzew, R., & Newkirk, M. M., *Clin Immunol Immunopathol* 71, 156–163 (1994)). In addition, levels of serum sCD23 in rheumatoid arthritis patients are related to disease status and correlate with serum rheumatoid factor (Bansal, A. S., et al., *Clin Exp Rheumatol* 12, 281–285 (1994)). Pro-inflammatory cytokines appear to be particularly important in rheumatoid arthritis, and a central role for TNF-α and IL-1β in the destruction of arthritic joints has been postulated (Brennan, F. M., Chantry, D., Jackson, A., Maini, R., & Feldman, M., *Lancet* 2, 244–247 (1989); Brennan, F. M., Maini, R. M., & Feldman M., *Br J Rheumatol* 31, 293–298 (1992)).

It has also been postulated that CD23-CD21 interactions may play a role in the control of IgE production (Flores-Romo L. et al., *Science* 261 1038–1041 (1993); Aubry et al., *Nature* 358, 505–507 (1992)).

CD11b and CD11c are adhesion molecules Fat participate in many cell-cell and cell-matrix interactions. CD11b/CD18 and CD11/CD18 (an association of CD11b and CD18 and of CD11c and CD18 respectively) have been reported to bind several ligands, including CD54, fibrinogen, factor X, LPS, Con A and zymosan (Springer, T. A., *Nature* 346, 425–434(1990)). The role of these binding molecules is not however completely understood. CD11b/CD18 and CD11c/CD18 are also known as MAC-1 and p150, 95 respectively. They are members of the β$_2$ integrin family (sometimes known as Leu-CAM, ie leucocyte cell adhesion molecules). This family also includes LFA-1 amongst its members (also known as CD11a/CD18).

EP 0205405 purports to disclose Mabs to lymphocyte cellular receptors for IgE (FCεR) cross reacting with human immunoglobulin E binding factor (IgE-BF), and derivatives thereof.

WO 93/04173 purports to disclose a polypeptide which is capable of binding to one of FCEL (low affinity IgE receptor FCεRII) or FCEH (high affinity receptor FCεRI) but which is substantially incapable of binding to the other of FCEL or FCEH. Treatment of an allergic disorder is alleged with a FCEL or FCEH specific polypeptide (provided the FCEH specific polypeptide is incapable of crosslinking FCEH and inducing histamine release).

EP 0269728 purports to disclose Mabs to the human lymphocyte IgE receptor.

EP 0259585 purports to disclose Mabs recognising a surface receptor for IgE (FCεR) on human B lymphocytes.

WO 93/02108 purports to disclose primatised antibodies for therapeutic use.

The present inventors have surprisingly discovered that binding agents to CD23 can be of utility in the treatment or prophylaxis of various diseases and in particular in the treatment or prophylaxis of arthritis. Prior to the present invention no data has been presented which would support such a utility, despite the publication of a large number of papers in which CD23 has been discussed.

According to the present invention, there is provided a binding agent to CD23 for use in the treatment or prophylaxis of inflammatory, autoimmune or allergic diseases.

The binding agent may function by blocking the interaction between CD23 and a ligand which binds to it. In vitro assays e.g. radioimmune assays may be used to study such a blocking effect The binding agent may be in isolated form or as part of a pharmaceutical composition. Desirably it is in sterile form. Generally speaking a binding agent which is specific for CD23 is useful in the treatment/prophylaxis disclosed.

The present inventors have demonstrated that binding agents within the scope of the present invention work in vivo in treatment or prophylaxis of inflammatory or autoimmune diseases.

This demonstration is of great significance, given the fact that many of these diseases are difficult or impossible to treat effectively, despite long standing research into their nature and causes. This is particularly the case in respect of arthritis, which often affects people in middle age and can cause them to give up work prematurely. An effective treatment of arthritis has been a long standing goal of many research groups.

Preferred binding agents include antibodies, fragments thereof or artificial constructs comprising antibodies or fragments thereof or artificial constructs designed to mimic the binding of antibodies or fragments thereof. Such binding agents are discussed by Dougall et al in *Tibtech* 12, 372–379 (1994).

They include complete antibodies, F(ab')$_2$ fragments, Fab fragments, Fv fragments, SCFv fragments, other fragments, CDR peptides and mimetics. These can be obtained/prepared by those skilled in the art. For example, enzyme digestion can be used to obtain F(ab')$_2$ and Fab fragments (by subjecting an IgG to molecule to pepsin or papain cleavage respectively). References to "antibodies" in the following description should be taken to include all of the possibilities mentioned above.

Recombinant antibodies may be used. The antibodies may be humanized; or chimaerised.

A typical preparation of a humanised antibody in which the CDRs are derived from a different species than the framework of the antibody's variable domains is disclosed in EP-A-0239400. The CDRs may be derived from a rat or mouse monoclonal antibody. The framework of the variable domains, and the constant domains, of the altered antibody may be derived from a human antibody. Such a humanised antibody elicits a negligible immune response when administered to a human compared to the immune response mounted by a human against a rat or mouse antibody.

Alternatively, the antibody may be a chimaeric antibody, for instance of the type described in WO 86/01533.

A chimaeric antibody according to WO 86/01533 comprises an antigen binding region and a non-immunoglobulin region. The antigen binding region is an antibody light chain variable domain or heavy chain variable domain. Typically, the chimaeric antibody comprises both light and heavy chain variable domains. The non-immunoglobulin region is fused at its C-terminus to the antigen binding region. The non-immunoglobulin region is typically a non-immunoglobulin protein and may be an enzyme region, a region derived from a protein having known binding specificity, from a protein toxin or indeed from any protein expressed by a gene. The two regions of the chimaeric antibody may be connected via a cleavable linker sequence.

The antibody may be a human IgG such as IgG1, IgG2, IgG3, IgG4; IgM; IgA; IgE or IgD carrying rat or mouse variable regions (chimaeric) or CDRs (humanised).

Primatizing techniques may also be used, such as those disclosed in WO93/02108.

As will be appreciated by those skilled in the art, where specific binding agents are described herein, derivatives of such agents can also be used. The term "derivative" includes variants of the agents described, having one or more amino acid substitutions, deletions or insertions relative to said agents, whilst still having the binding activity described. Preferably these derivatives have substantial amino acid sequence identity with the binding agents specified.

The degree of amino acid sequence identity can be calculated using a program such as "bestfit" (Smith and Waterman, Advances in Applied Mathematics, 482–489 (1981)) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M.O., Ed pp 353–358.

Preferably the degree of sequence identity is at least 50% and more preferably it is at least 75%. Sequence identities of at least 90% or of at least 95% are most preferred.

It will nevertheless be appreciated by the skilled person that high degrees of sequence identity are not necessarily required since various amino acids may often be substituted for other amino acids which have similar properties without substantially altering or adversely affecting certain properties of a protein. These are sometimes referred to as "conservative" amino acid changes. This the amino acids glycine, valine, leucine or isoleucine can often be substituted for one another (amino acids having aliphatic hydroxyl side chains). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains) and cysteine and methionine (amino acids having sulphur containing side chains). Thus the term "derivative" can also include a variant of an amino acid sequence comprising one or more such "conservative" changes relative to said sequence.

The present invention also includes fragments of the binding agents or of the present invention or of derivatives thereof which still have the binding activity described. Preferred fragments are at least ten amino acids long, but they may be longer (e.g. up to 50 or up to 100 amino acids long).

The binding agents of the present invention are believed to be useful in the treatment or prophylaxis of several human diseases including arthritis, lupus erythematosus, Mashimotos thyroiditis, multiple sclerosis, diabetes, uveitis, dermatitis, psoriasis, urticaria, nephrotic syndrome, glomerulonephritis, inflammatory bowel disease, ulcerative colitis, Crohn's disease, Sjogren's syndrome, allergies, asthma, rhinitis, eczema, GVH, COPD, insulitis, bronchitis (particularly chronic bronchitis) or diabetes (particularly Type 1 diabetes).

They may also be useful in studying the interactions between CD23 and various ligands e.g. between CD23 and CD21, between CD23 and CD11b, between CD23 and CD11c, between CD23 and a 70 to 85 KDa endothelial cell protein (which may be a 76, 80 or 85 KDa endothelial cell protein) or between CD23 and a 115 KDa endothelial protein (which is believed to be related to the 70 to 85 KDa endothelial protein). One or more of the above interactions are believed to occur, in vivo. Antibodies or other binding agents which are capable of blocking these interactions are particularly preferred since it is believed that they may be especially suitable for reducing or alleviating cytokine mediated inflammatory effects. They may also be useful against B-cell malignancies such as chronic lymphocytic leukaemia, and hairy cell leukaemia.

Binding agents of the present invention are particularly applicable for use in the treatment or prophylaxis of rheumatoid arthritis. Without being bound by theory, the following possible explanations are put forward:

In the rheumatoid arthritis inflamed synovium, macrophages express both CD23 and the $\beta_2$ integrins CD11b and CD11c, allowing possible homotypic interactions to take place in this tissue. In addition, diffusion of soluble CD23 molecules through the synovium and their binding to the integrin ligands is also possible. Therefore, CD23CD11b/CD11c interactions involving a positive activation loop could exist in vivo. If present in rheumatoid arthritis patients, it may explain some of the pathogenic mechanisms of disease exacerbation and chronicity, and would support the hypothesis once localised to the joints, macrophages themselves can maintain and exacerbate inflammation via a pathway involving CD23 molecules, $\beta_2$-integrins CD11b and CD11c, as well as pro-inflammatory cytokines TNF-$\alpha$, IL-1$\beta$ and IL-6.

An alternative mechanism of action of anti CD23 therapy could involve the blocking of an IgE immune response.

In previously published work it has been shown that in vivo treatment of rats with anti-CD23 antibody resulted in antigen-specific inhibition of IgE production, probably by blocking the CD23-CD21 interactions necessary for complete differentiation of IgE-committed B cells (Flores-Romo et al., *Science* 261, 1038–1041 (1993)).

The present invention also includes binding agents to CD23 which block such a response.

Structurally, the CD21 protein is composed of an extra-cellular domain of 15 (Moore et al, Molecular cloning of the cDNA encoding the Epstein Barr Virus C3d receptor (complement receptor type 2) of human B lymphocyte, *Proc Natl Acad Sci USA* 84: 9194 (1987)) or 16 (Weis et al, Structure of the human B lymphocyte receptor for C3d and the Epstein Barr Virus and relatedness to other members of the family of C3/C4 binding proteins, *J Exp Med* 167: 1047 (1988)) repetitive units of 60 to 75 amino acids, named short consensus repeats (SCRs), followed by a transmembrane domain (24 amino acids) and an intracytoplasmic region of 34 amino acids. Using CD21 mutants bearing deletions of extracytoplasmic SCRs (Carel et al, Structural requirements for C3d,g/Epstein Barr Virus receptor (CR2/CD21) ligand binding, internalization, and viral infection *J Biol Chem* 265: 12293 (1990)), the present inventors have recently found that CD23 binds to SCRs 5–8 and 1–2 on CD21. The binding of CD23 to SCRs 5–8 is a lectin-like interaction, involving carbohydrates on Asn 295 and 370. In contrast, CD23 binding to SCRs 1–2 is a protein-protein interaction (Aubry et al, CD23 interacts with a new functional extracytoplasmic domain involving N-linked oligosaccharides on CD21. *J Immunol* 152: 5806 (1994)). The present inventors have now tested the effect of the other ligands of CD21 (EBV, C3d,g and IFN-α) on CD23 binding to CD21 and on the regulation of Ig production in the presence of IL-4. Only EBV particles and an EBV-derived peptide were able to inhibit CD23 binding to CD21. Moreover, the EBV-peptide selectively decreased IgE and IgG4 production and increased IgM production. These data indicate that CD23 binding to the EBV-binding site on CD21 selectively regulates human Ig production in the presence of IL-4.

Again without being bound by theory, it is believed that the present invention allows effective treatments to be achieved by suppressing the de novo synthesis of pro-inflammatory cytokines.

This contrasts with previous uses of antibodies simply to directly neutralise the cytokine molecules already present in inflamed tissues.

It should also be noted that there are speculative publications in the art listing large numbers of antibodies as well as large numbers of possible diseases which the antibodies are said to be useful in treating, but not providing any sound evidence or data for most of the possible combinations. One such publication is WO93/02108 which is primarily directed to the production of particular chimaeric antibodies.

The present invention is clearly distinguished from such publications by providing binding agents to particular molecules which are clearly indicated to be of utility in the treatment or prophylaxis of certain diseases in view of the data and explanations provided herein.

Binding agents of this invention are also of particular use in the treatment or prophylaxis of allergic diseases, including non-IgE mediated diseases. They may be used in the treatment and propylaxis of ulcerative colitis. They may also be used in the treatment and prophylaxis of Crohn's disease.

The binding agents of the present invention may be used alone or in combination with immunosuppressive agents such as steroids, cyclosporin, or antibodies such as an anti-lymphocyte antibody or more preferably with a tolerance-inducing, anti-autoimmune or anti-inflammatory agent such as a CD4+T cell inhibiting agent e.g. an anti-CD4 antibody (preferably a blocking or non-depleting antibody), an anti-CD8 antibody, a TNF antagonist e.g. an anti-TNF antibody or TNF inhibitor e.g. soluble TNF receptor, or agents such as NSAIDs.

The binding agent will usually be supplied as part of a sterile, pharmaceutically acceptable composition This pharmaceutical composition may be in any suitable form, depending upon the desired method of administering it to a patient. It may be provided in unit dosage form and may be pro ed as part of a kit. Such a kit would normally (although not necessarily) include instructions for use.

Binding agent administrations are generally given parenterally, for example intravenously, intramuscularly or subcutaneously. The binding agents are generally given by injection or by infusion. For this purpose a binding agent is formulated in a pharmaceutical composition containing a pharmaceutically acceptable carrier or diluent. Any appropriate carrier or diluent may be used, for example isotonic saline solution. Stabilizers may be added such as a metal chelator to avoid copper-induced cleavage. A suitable chelator would be EDTA, DTPA or sodium citrate.

They may be given orally or nasally by means of a spray, especially for treatment of respiratory disorders.

They may be formulated as creams or ointments, especially for use in treating skin disorders.

They may be formulated as drops, or the like, for administration to the eye, for use in treating disorders such as vernal conjunctivitis.

For injectable solutions, excipients which may be used include for example, water, alcohols, polyols, glycerine, and vegetable oils.

The pharmaceutical compositions may contain preserving agents, solubilising agents, stabilising agents, wetting agents, emulsifiers, sweeteners, colourants, odourants, salts, buffers, coating agents or antioxidants. They may also contain other therapeutically active agents.

Suitable dosages of the substance of the present invention will vary, depending upon factors such as the disease or disorder to be treated, the route of administration and the age and weight of the individual to be treated. Without being bound by any particular dosages, it is believed that for instance for parenteral administration, a daily dosage of from 0.01 to 50 mg/kg of a binding agent of the present invention (usually present as part of a pharmaceutical composition as indicated above) may be suitable for treating a typical adult. More suitably the dose might be 0.05 to 10 mg/kg, such as 0.1 to 2 mg/kg.

This dosage may be repeated as often as appropriate. Typically administration may be 1 to 7 times a weeks. If side effects develop the amount and/or frequency of the dosage can be reduced.

A typical unit dose for incorporation into a pharmaceutical composition would thus be at least 1 mg of binding agent, suitably 1 to 1000 mg.

The present invention includes within its scope an assay for determining whether or not a particular agent which binds to CD23 may be useful in the treatment of an inflammatory, autoimmune or allergic disease comprising: determining whether or not the agent is capable of blocking the interaction between CD23 and CD11b, or the interaction between CD23 and CD11c, or the interaction between CD23 and CD21, or the interaction between CD23 and a 70 to 85 KDa (such as a 76 KDa, 85 KDa or 80 KDa) or a 115 KDa protein expressed on endothelial cells.

This assay can be used for screening compounds or molecules by using cell lines expressing the appropriate molecules. Preferably CD11b is used in these assays as CD11b/CD18 and CD11c is used as CD11c/CD18. CD11b/CD18 and CD11c/CD18 can be co-expressed on cell surface.

Any appropriate assay technique can be used, e.g. protein-non protein assays (e.g. assaying the interaction of proteins with chemicals or sugars), protein-protein assays or protein-cell assays.

BRIEF DESCRIPTION OF THE DRAWINGS

The present invention will now be described by way of example only with reference to the accompanying drawings; wherein.

EXAMPLES (In some of the following examples the terms "ip", "id" and "n" are used. These mean "intraperitoneal", "intradermal" and "number of animals" respectively.)

Example 1

Preventative Treatment of Mice against Arthritis Using Anti-CD23 Antibody

Male DBA/1 mice (8–12 weeks old) were sedated with 0.1 ml of a 1:10 dilution of Fentanyl/Fluanisol 'Hypnorm' ip and injected intradermally at the base of the tail with 100 mg bovine type II collagen (CII) emulsified in Freund's complete adjuvant (Difco). On day 13 post-CII immunisation, test mice were treated with one single injection of rabbit anti-CD23 IgG purified by protein-A Sepharose (Bio-Processing, UK) (2 mg/mouse, ip) (n=16, ■——■). The purified anti-CD23 IgG contains 3–5% specific antibody.

A detailed description of its production is given in Flores-Romo L et al., Science 261 1038–1041 (1993). Briefly, a rabbit polyclonal antibody was raised to a truncated form of human CD23 corresponding to amino acids 150 to 321 of full length CD23 [Kikutani et al. Cell 47 657 (1986)]. The truncated polypeptide was produced in E coli and purified from a washed pellet of E. coli by ion-exchange and gel filtration. It had a molecular weight of 25 kD and after purification was injected into a rabbit. The resultant antiserum tested positive in both an ELISA and a protein immunoblot with recombinant human CD23. An IgG fraction was then isolated by protein A-Sepharose affinity chromatography. Control animals received protein-A purified IgG from normal rabbit serum (2 mg/mouse) (n=17, ●-----●). Mice were inspected daily for development of clinical symptoms of arthritis. The severity of disease was scored on each paw using a scale from 0=no symptoms to 3=pronounced swelling erythema and impairment of movement as described in Williams et al., Proc. Natl. Acad. Sci. USA 89 9784–9788 (1992); limb recruitment was assessed by counting the number of affected paws. Groups were compared by statistical analysis using the two-tailed t-test in (a), and the non-parametric Mann-Whitney test in (b), *$0.05 \geq p > 0.01$, $0.01 \geq p > 0.005$, *$0.005 \geq p$.

Figure 1A:
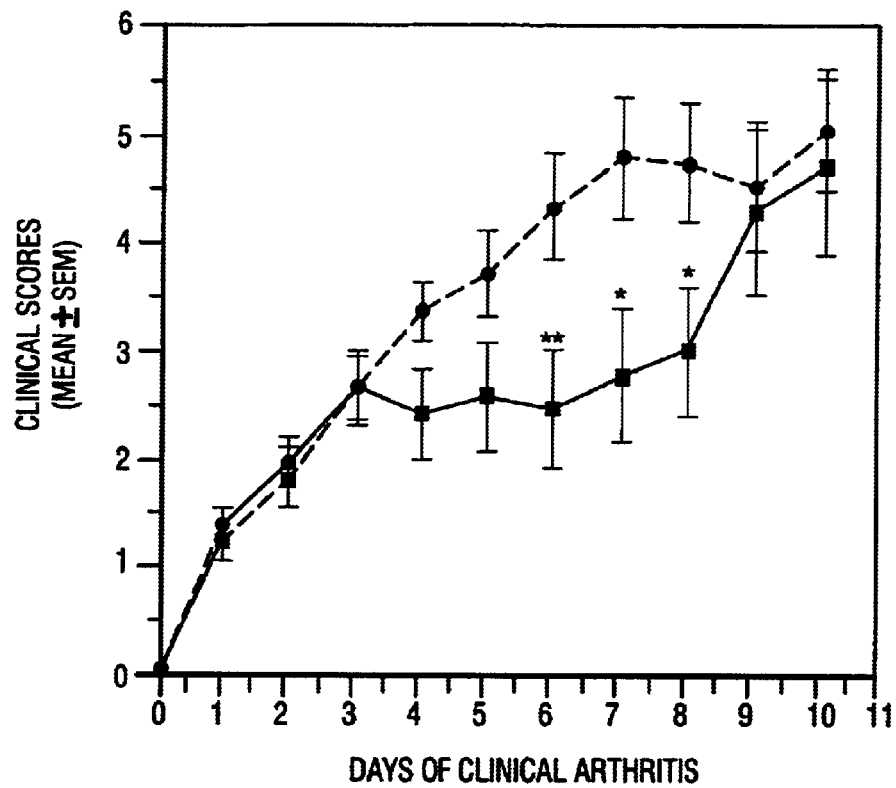
FIGS. 1A and 1B illustrate the effect of preventative treatment against arthritis on mice using an anti-CD23 antibody.
Figure 1B:
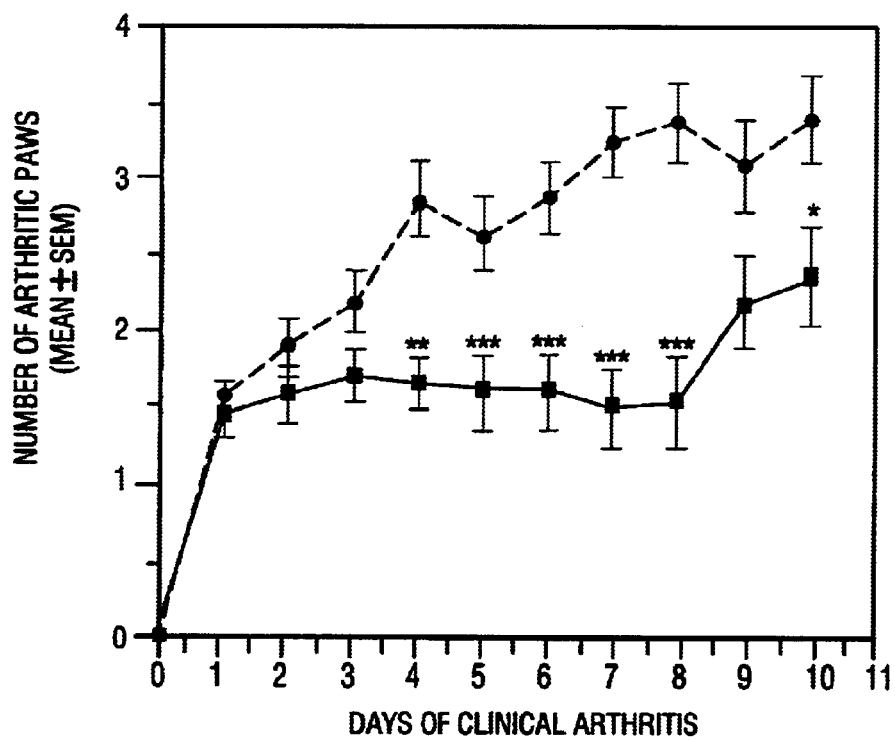

No difference in disease onset was observed (median day of onset+sem: 20+0.7 in test group and 20 0.5 in the control group) or incidence of disease (100% arthritic mice in both groups), demonstrating that treatment with anti-CD23 antibody had no effect on disease induction at the time of T-cell proliferation and IgG anti-collagen antibody induction. However, the overall clinical scores were lower in mice treated with anti-CD23 antibody (FIG. 1a). Most notable was the marked suppression of limb recruitment in the anti-CD23 treated group (FIG. 1b). These results indicate a strong influence of the treatment on the long-term progression of the disease.

Example 2

Treatment of Established Arthritis (Multiple Treatments)

Figure 2A:
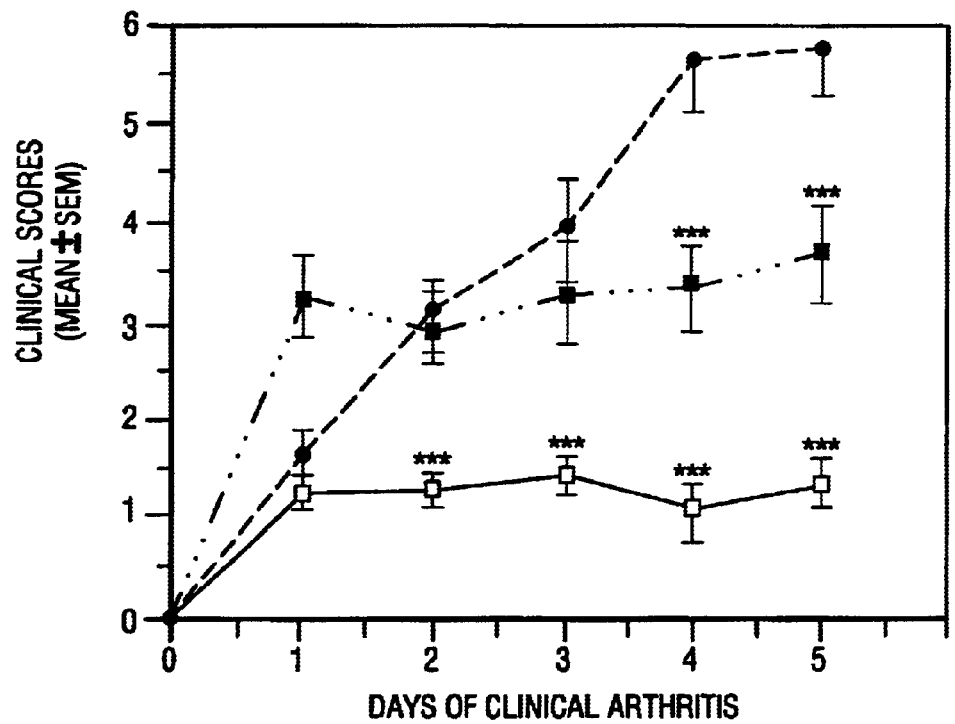
FIGS. 2A and 2B illustrate the effect of the treatment of mice with an anti-CD23 antibody in respect of established arthritis, where multiple treatments of the antibody are used.
Figure 2B:
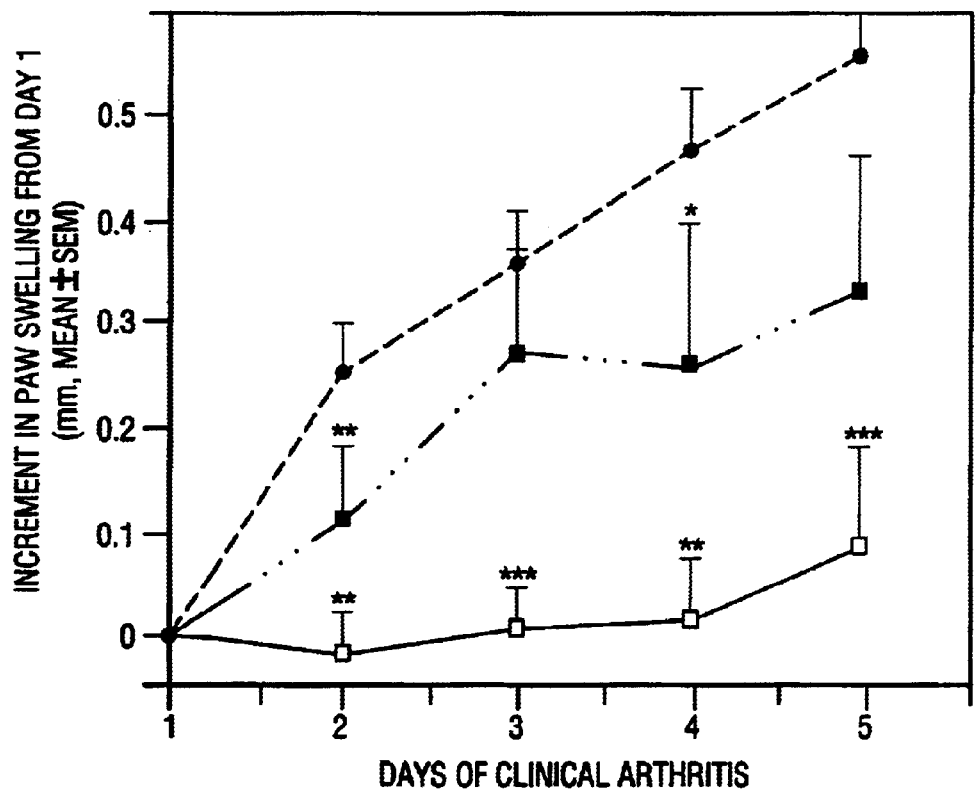

Arthritis was induced as disclosed for Example 1 and mice were monitored daily for development of visible inflammation. Treatment was administered on first day of clinical inflammation (day 1) and two days later (day 3) on randomly divided three groups of mice. Test mice received protein-A purified anti-CD23 IgG (200 μg/injection, n=6, ■----■; 400 μg/injection, n=8 ■——■; control mice received protein-A purified normal rabbit IgG (200 μg/injection, n=15, ●-----●). Severity of disease (FIG. 2a) was assessed as described in Example 1. Inflammation was assessed by the incremental swelling from day 1 of the first paw to become arthritic measured using callipers (Proctest 2T. Kroeplin Langenmesstechnik). Groups were compared using the two-tailed t-test, *$0.05 \geq p > 0.01$, $0.01 \geq p > 0.005$, *$0.0005 \geq p$.

Marked improvement in disease severity can be seen, which is dose related. The anti-inflammatory property of anti-CD23 IgG is clearly demonstrated by reduced paw swelling in the group of mice receiving antibody treatment.

Example 3

Treatment of Established Arthritis (Single Treatment)

Experiment design was similar to Example 2 with the exception that mice were treated only once, on day 1 of arthritis, with 2 mg/mouse of protein-A purified anti-CD23 IgG (n=10, ■——■) or purified normal rabbit IgG (n=10, ●----●). Clinical scores and limb recruitment was assessed as for Example 1.

Figure 3A:
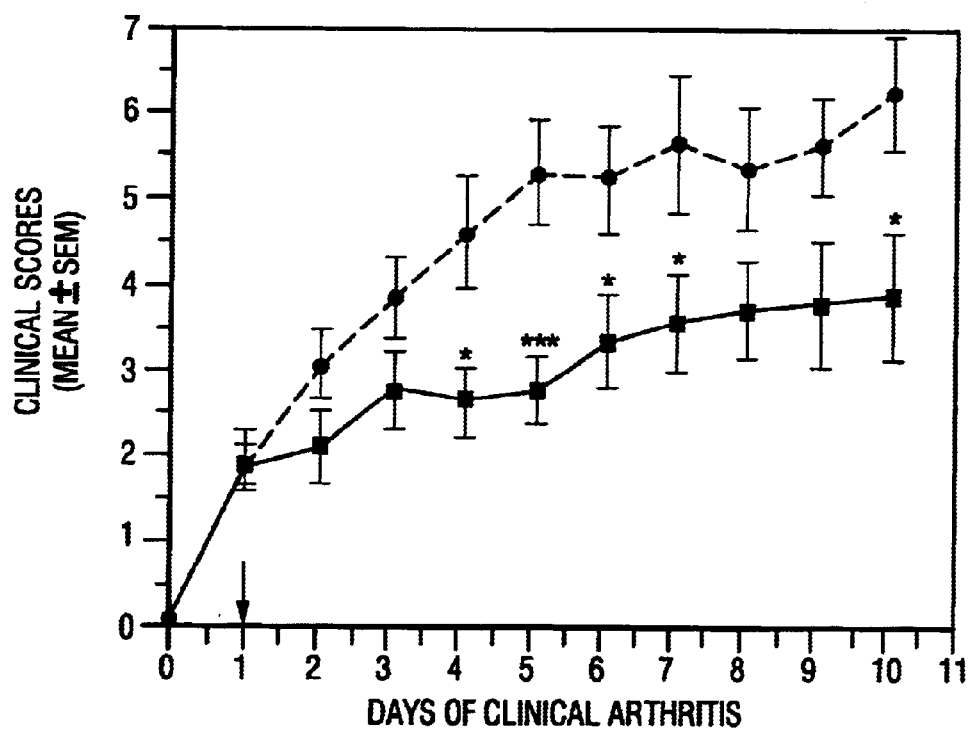
FIGS. 3A and 3B illustrate the effect of the treatment of mice with an anti-CD23 antibody in respect of established arthritis where a single treatment is used.
Figure 3B:
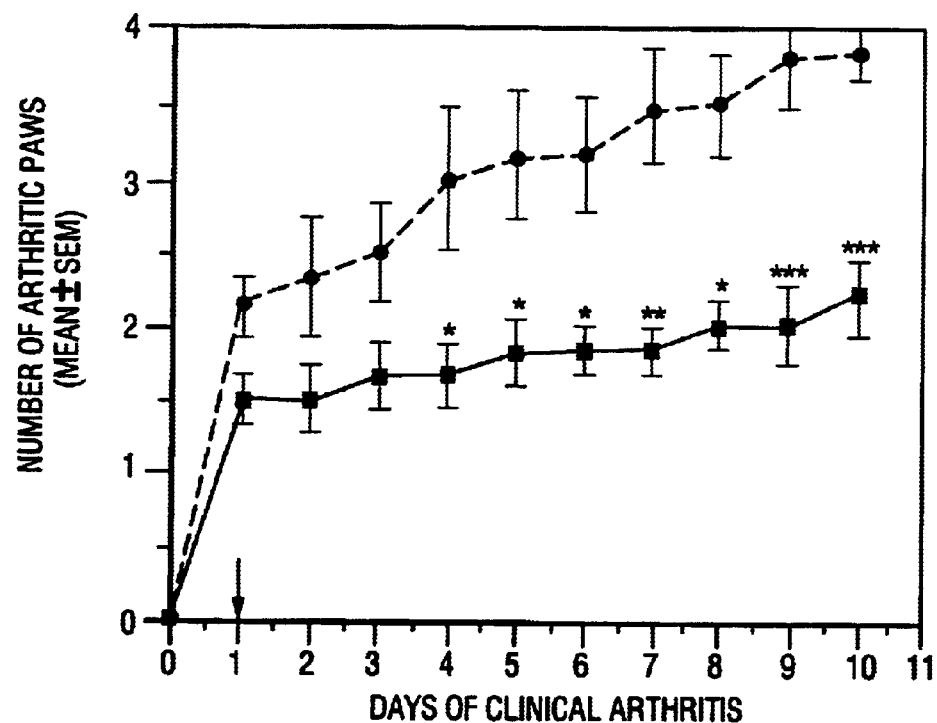

The significant effect on limb recruitment obtained after one injection on day 1 demonstrates that in terms of joint recruitment a single injection administered when arthritis is already established is sufficient to protect against further disease progression (FIG. 3b).

Example 4

Treatment of Established Arthritis with Monoclonal Anti-CD23

Arthritic DBA/1 mice were obtained as described above for Example 1. On first sign of clinical disease mice were separated randomly in four groups and treated on days 1 and 3 with three doses of monoclonal antibody to CD23 (B3B4, kindly donated by Professor D. Conrad, Richmond, Va., USA and obtainable from Pharmingen. It is discussed in *J Immunol* 138: 1845–1851 (1987)); B3B4 25 µg/injection, n=4 o·······o, B3B4 50 µg/injection, n=4; ■----■; B3B4 100 µg/injection, n=5. ■——■). Control mice received PBS (n=6●----●). Clinical scores and increment in paw thickness from day 1 were assessed as described for Example 2.

Figure 4A:
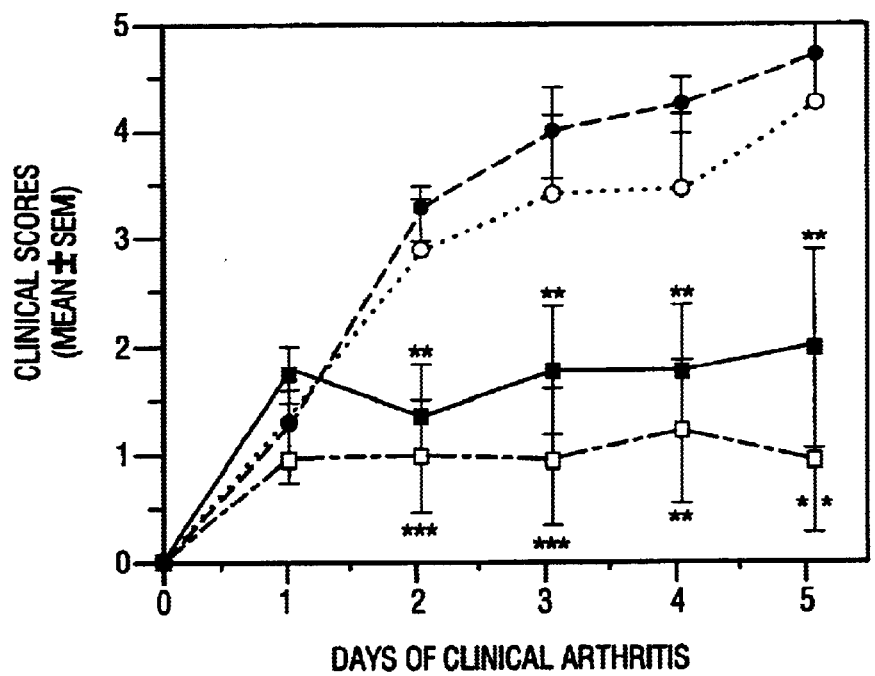
FIGS. 4A and 4B illustrate the effect of the treatment of mice with a monoclonal anti-CD23 antibody in respect of established arthritis where multiple treatments are used.
Figure 4B:
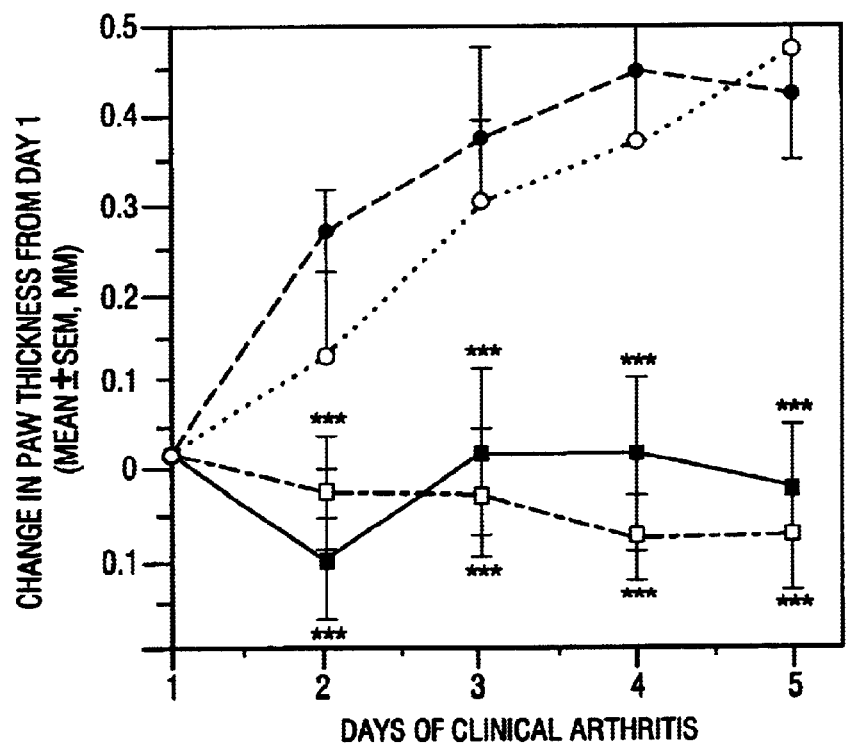

Intraperitoneal injections of 50 µg of B3B4 monoclonal antibody were sufficient for effective therapy as shown by the significant decrease in clinical scores and the number of affected paws obtained using this treatment regimen. In contrast, the disease severity of mice treated with 25 µg monoclonal antibody did not improve the positive therapeutic effect obtained with 50 µg B3B4 monoclonal antibody (FIG. 4). The dose-related anti-inflammatory effect of B3B4 administration is illustrated in FIG. 4b which shows that swelling of the arthritic paws did not increase from day 1 in the groups receiving ip injections of 50 or 100 µg monoclonal antibody B3B4. Similarly to what was observed with the other clinical measurements, doses of 25 µg monoclonal at CD23, administered after disease onset, were sub-therapeutic and the increments in paw swelling were similar to controls (FIG. 4b). Likewise, a significant reduction in severity of the established arthritis was obtained after treatment with 50 µg affinity purified polyclonal anti-CD23 IgG (data not shown).

The improvement in clinical severity following treatment with anti-CD23 antibody (both monoclonal and polyclonal) was confirmed by histological examination of the arthritic paws. Treated mice showed reduced severity of disease with less apparent destruction of cartilage and bone and a marked decrease in cellular infiltration of the sublining layer of the synovium. Moreover, the proportion of severely affected joints was significantly lower in anti-CD23 antibody treated animals in comparison to control mice (0% vs 94%), whereas the proportion of joints maintaining normal structure was significantly increased (80% vs 0%).

This is demonstrated in Table 1 below:

TABLE 1

Histopathology of paws: Mice were treated and joints processed as in FIG. 4. Histological preparations were scored as described in methodology.

| Treatment (no of mice) | Normal (%) | Mild (%) | Moderate (%) | Severe (%) | Total number of joints examined |
|---|---|---|---|---|---|
| anti-CD23 (n = 6) | 80 | 8 | 12 | 0 | 59 |
| controls (n = 6) | 0 | 0 | 6 | 94 | 69 |

This table shows a comparison of histological preparations in respect of joints taken from mice treated with anti-CD23 or from control mice. The mice had been treated as described above in relation to FIG. 4.

Histopathology was assessed as follows:

The first limb to become arthritic was removed postmortem, fixed in 10% (wt/vol) buffered formalin and decalcified in EDTA in buffered formalin (5.5%). The paws were then embedded in paraffin, sectioned and stained with haematoxylin and eosin. Histological preparations (3 sections/paw) were scored using the following criteria: mild+minimal synovitis, cartilage loss and bone erosions limited to discrete foci; moderate=synovitis and erosions present but joint architecture intact; severe=extensive synovitis and erosions with disruption of join architecture. All the joints present in each section were assessed and the percentage presenting normal, mild, moderate or severe scores was determined. Inflammation was assessed by the increment in paw thickness relative to the thickness of the paw on the first day of treatment, measured using calipers (Proctest 2T, Kroeplin Langenmesstechnik).

Further evidence to support specificity of this treatment was obtained by treating arthritic mice with Fab and F(ab')$_2$ fragments of B3B4 monoclonal antibody. Although less potent than the intact IgG molecule, Fab and F(ab')$_2$ fragments of B3B4 were still effective thus demonstrating that the Fc portion of the antibody is not compulsory for the activity (Table 2). Moreover, antibodies to CD72 and B220 molecules, both highly expressed on B lymphocytes, showed little to no therapeutic activity (Table 2). In addition comparison with antibodies to TNF-α (Williams et al *Proc Natl Acad Sci USA* 36: 9784–9788 (1992)) and CD5 (Plater-Zyberk et al *Clin Exp Immunol* 98: 442447 (1994)) showed that in our experimental conditions, anti-CD23 antibody treatment was the most effective (Table 2).

TABLE 2

Comparison in the response to different treatment regimen: Mice were immunised with type II collagen and treated therapeutically on day 1 and 3 of clinical arthritis by i.p. injection of monoclonal antibodies. The decrease in clinical scores on day 5 was calculated as a percentage of the isotype control used in each experiment.

| Mab | Clone | Treatment dose | Isotype | Decrease in clinical scores (%) |
|---|---|---|---|---|
| CD23 | B3B4 | 50 µg × 2 | Rat IgG2a | 74 |
|  |  | 75 µg × 2 | Rat F(ab)$_2$ | 52 |
|  |  | 150 µg × 2 | Rat Fab | 56 |
| TNF-α | 1F3F3D4 | 50 µg × 2 | Rat IgM | 63 |
| CD5 | TIB 104 | 200 µg × 2 | Rat IgG2a | 30 |
| B220 | TIB 146 | 200 µg × 2 | Rat IgM | 5 |
| CD72 | TIB 165 | 200 µg × 2 | Mouse IgG2b | 0 |

Figure 4C:
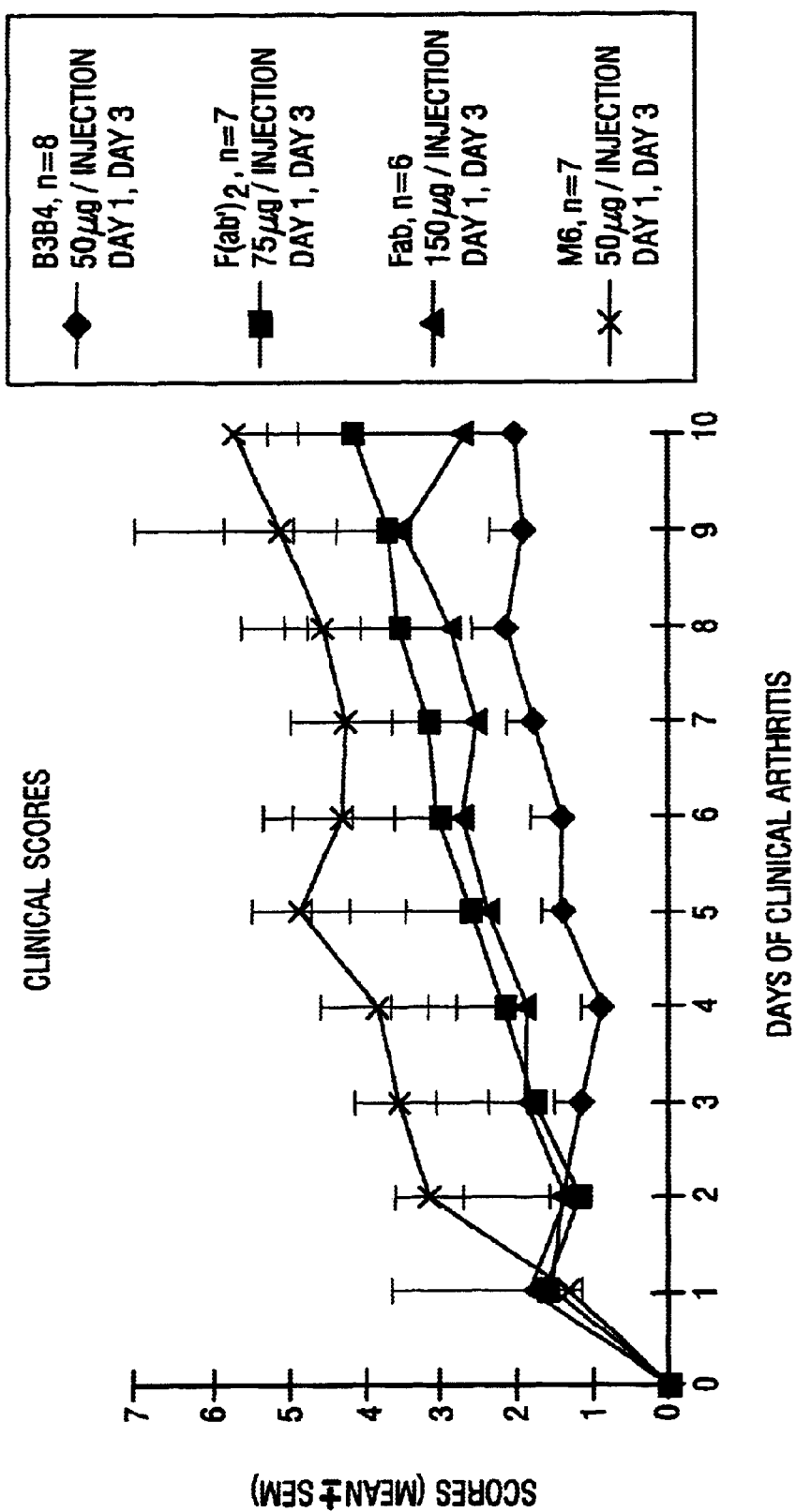
FIGS. 4 c) and d) illustrate the effect the treatment of mice with F(ab')$_2$ and Fab fragments of a monoclonal anti-CD23 antibody in respect of established arthritis where multiple treatments are used.
Figure 4D:
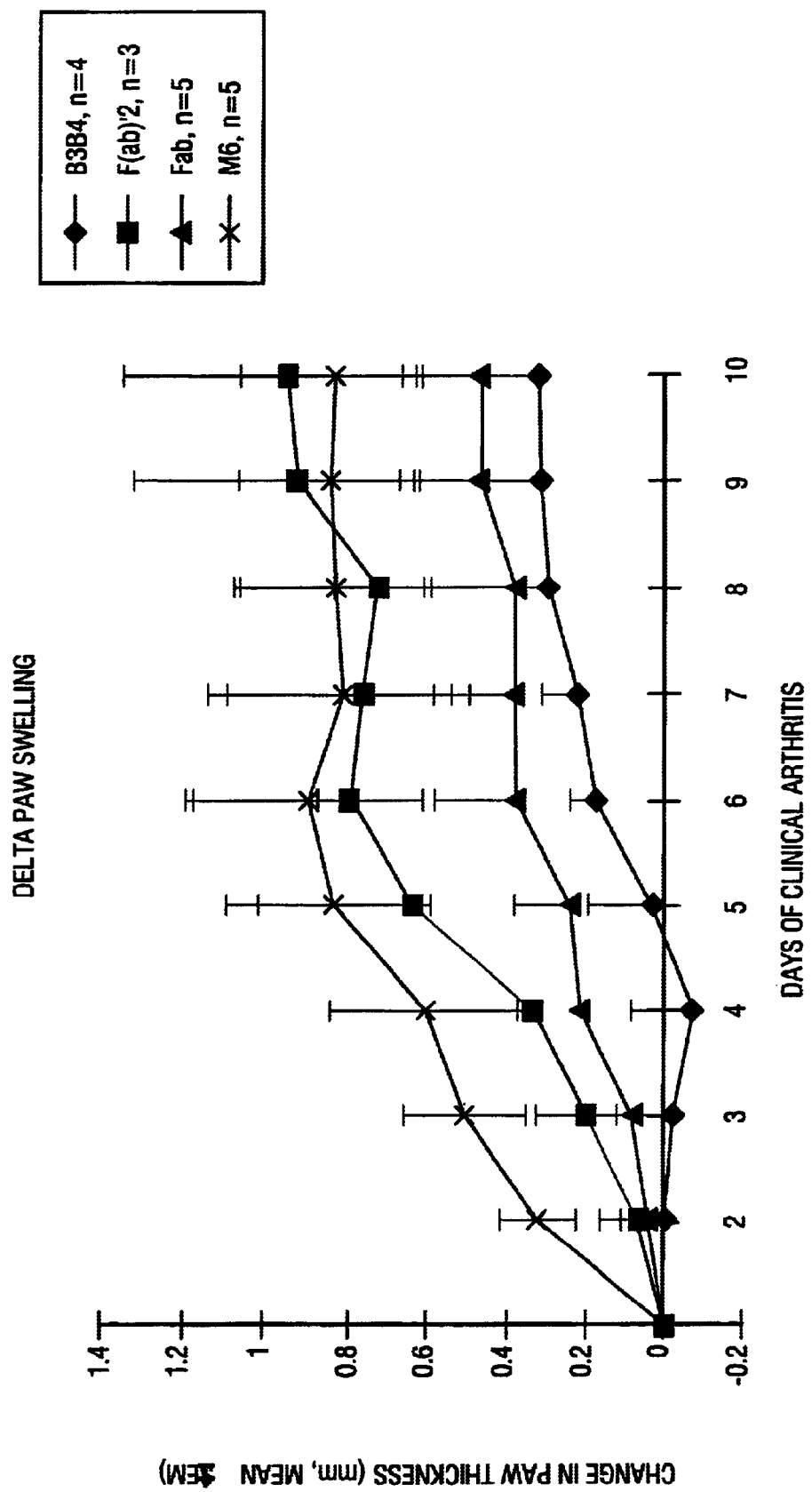

Further data in respect of monoclonal antibodies and fragments thereof are provided in FIGS. 4c and 4d. Those data are based upon the following protocol:

Male 8–12 weeks old DBA/1 mice injected id with 100 µg bovine type II collagen emulsified in complete Freund's adjuvant.

On first sign of clinical disease (±3 weeks later) mice are injected ip with the following preparations of monoclonal antibodies, (injections on day 1 and day 3)

| B3B4 whole IgG 2a | 50 µg/injection ip n = 8 |
|---|---|
| Fab of B3B4 | 150 µg/injection ip n = 6 |
| F(ab')$_2$ of B3B4 | 75 µg/injection ip n = 7 |
| M6 control IgG2a | 50 µg/injection ip n = 7 |

Mice are inspected daily and severity of clinical disease of each paw is scored (max/paw=3; max/mouse=12). The results for the scoring of clinical disease are shown in FIG. 4c.

The swelling of the first arthritic paw is followed using calipers. The results for the scoring of paw swelling are shown in FIG. 4d.

Mice are killed on day 10 of arthritis, the first paw to become arthritic is sectioned, fixed and decalcified for histopathological examination.

Interaction between CD23 and CD11b and between CD23 and CD11c

Without wishing to be bound by theory, since it is not fully understood how anti-CD23 antibodies achieve the surprising results disclosed above, it is possible that this may be due to the interaction of CD23 with CD11b and/or CD11c. Examples 5 to 10 and the accompanying Figures (see later) illustrate this. In these Examples, full-length recombinant CD23 incorporated into fluorescent liposomes was shown to bind to COS cells transfected with cDNA encoding either CD11b/CD18 or CD11c/CD18 but not with transfectants expressing CD11a/CD18. The interaction between CD23-liposomes and CD11b/CD18 or CD11c/CD18-transfected COS cells was specifically inhibited by anti-CD11b or anti-CD11c, respectively, and by anti-CD23 monoclonal antibodies. The functional significance of this ligand pairing was demonstrated by triggering CD11b and CD11c on monocytes with either recombinant CD23 or anti-CD11b and anti-CD11c monoclonal antibodies to cause a marked increase in nitrite ($NO_2^-$) oxidative products ($H_2O$) and proinflammatory cytokines (IL-1$\beta$, IL-6 and TNF$\alpha$). These CD23-mediated activities were decreased by Fab fragments of monoclonal antibodies to CD11b, CD11c and CD23. These results demonstrate that the surface adhesion molecules CD11b and CD11c are receptors for CD23 and that this novel ligand pacing regulates important activities of monocytes.

The following discussion explains briefly the experimental design and the rationale behind Examples 5 to 10 (which follow):

Total blood mononuclear cells were incubated with recombinant full-length CD23 incorporated into fluorescent liposomes and analysed by flow cytometry (Pochon, S. et al. *J. Exp. Med.* 176, 380–398 (1992)). A fraction bound CD23-liposomes (Example 5, FIG. 5a) which was then shown by double staining to consist of CD14positive cells (i.e. monocytes). To confirm that monocytes were able to bind CD23-liposomes, blood mononuclear cells were FACS-sorted into CD14-positive and CD14-negative populations (Example 5, FIG. 5a) CD23-liposomes were shown to bind only to the CD14-positive population (Example 5, FIG. 5a). Since monocytes were Wound to express neither membrane IgE nor CD21 (not shown), the known ligands for CD23, it fleas investigated whether monocytes express a different receptor or CD23. Monocytes were lysed and cell extracts purified over an affinity column coupled with recombinant soluble CD23. SDS-PAGE and silver strong analysts of the eluted material revealed bands of around 80 and 160 kDa MW (Example 5, FIG. 5b). Antibodies identifying antigens within this range of MW and reported to be expressed on monocytes were tested by FAGS for their capacity to inhibit CD23-liposome binding to monocytes (Example 6, FIG. 6). Anti-CD11b and anti-CD11c monoclonal antibodies both inhibited CD23-liposome binding to monocytes, with varying degrees of potency (Example 6, FIG. 6). Anti-CD13, anti-CD49d, anti-CD21 (not expressed on monocytes) and anti-CD11a (the third member of the $\beta$2 integrin family of adhesion molecules) had no significant effect (Example 6, FIG. 6). Antibodies against MHC Class I, Class II, CD14 and CD45, all of which highly expressed on monocytes were also tested for their effect on CD23-liposome binding. None however had any effect (not shown). Anti-CD18 monoclonal antibody gave a partial inhibition of CD23 binding. This could be due either to steric hindrance or to the induction of a conformational change in the CD11b and CD11c molecules upon CD18 Mab binding. The monocyte-derived proteins eluted from the CD23-affinity column were immunoreactive with anti-CD11c (Example 5, FIG. 5b) and anti-CD11c/CD18 antibodies (not shown).

To confirm that the $\alpha$ chain of CD11b/CD18 and CD11c/CD11b were receptors for CD23, full-length cDNAs encoding CD11b and CD11c were transiently co-transfected with CD18 cDNA into COS cells. Transfectants expressing CD11b/CD18 and CD11c/CD18 were both shown to bind CD23-liposomes, in contrast to transfectants expressing CD11a/CD18 (Example 7, FIG. 7). This might be explained by the higher degree of homology between CD11b and CD11c when compared to the homology to CD11a. The specificity of the interaction was demonstrated by inhibiting CD23-liposome binding using anti-CD11b, anti-CD11c and anti-CD23 monoclonal antibodies. The same results were obtained using BHK cells expressing CD11b/CD18 and CD11c/CD18 (not shown). As further proof of the specificity of the CD23 interaction, activated blood monocytes from a Leukocyte Adhesion Deficiency patient, lacking $\beta$2 integrin expression due a mutation in the gene encoding the $\beta$ subunit were unable to bind CD23-liposomes (not shown). Together, these data demonstrate that CD23 interacts with CD11b and CD11c on normal human monocytes and on transfectants.

Figure 8:
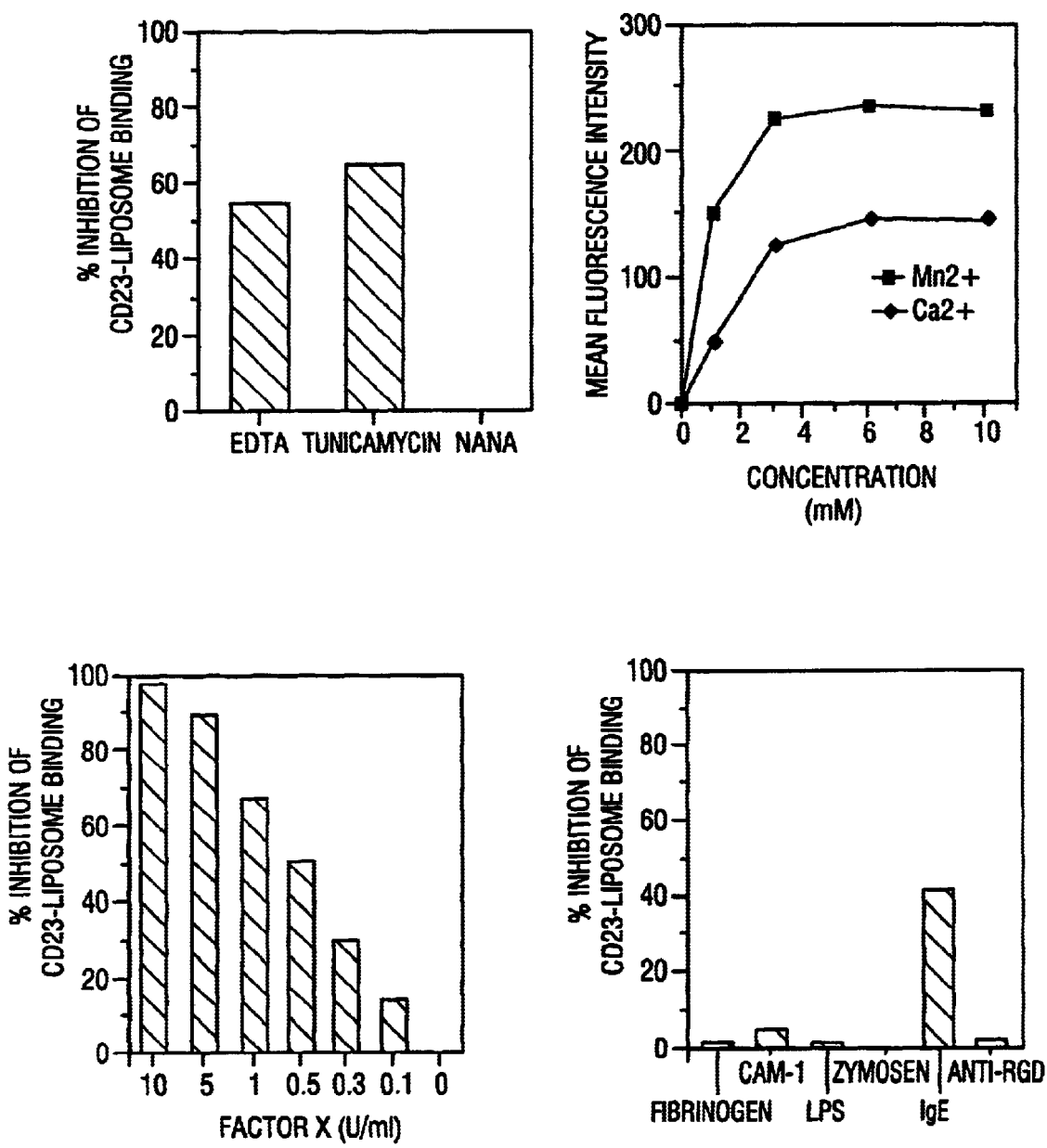
FIG. 8 illustrates the effect of various substances on CD23-CD11b and CD23-CD11c interaction.

CD11b and CD11c are adhesion molecules that participate in mary cell-cell and cell-matrix interactions. The examples show that CD11b/CD18 and CD11d/CD18 may exhibit an additional adhesive function by virtue of their ability to bind CD23. CD23 seems to identify an epitope dose or identical to factor X as observed by the capacity of factor X to inhibit in a dose dependent manner CD23-liposome binding (Example 8, FIG. 8) without affecting surface expression of CD11b or CD11c on monocytes (not shown). None of the other ligands tested had any effect CD23 may be acting as a C-type lectin in its interaction with CD11b and CD11c. EDTA decreases CD23 binding to monocytes (Example 8, FIG. 8) by chelation of $Ca^{2+}$ which is necessary to CD23 binding and/or by chelation of the divalent cations which are necessary for the binding of ligands to CD11b and CD11c (Altieri, D. C. *J. Immunol.* 147, 1891–1898 (1991)). CD23-CD11b/CD11c interaction seems to involve sugars, but not sialic acid, as observed by the capacity of tunicamycin, but not neuraminidase, to decrease CD23 binding to monocytes. CD23 bears extracellularly a triplet of amino acids (Asp, Gly, Arg) (Kikutani, H. et al. *Cell* 47, 867–885 (1986)), which in the reverse orientation is a common recognition site for the integrin receptors. Therefore, the effect of a polyclonal antibody directed against this tripeptide was tested for its capacity to inhibit CD23 binding to monocytes. No inhibition was observed, confirming the absence of inhibition obtained with fibrinogen (Example 8, FIG. 8). IgE which is binding in the lectin domain of CD23, partially inhibits CD23 binding to monocytes (Example 8, FIG. 8). Those results indicate that CD23 would seem to be acting as a C-type lectin recognising partly sugar and protein structures, reminiscent of what has been observed for CD23 interaction with CD21 (Aubry, J-P. et al. *J. Immunol.* 152, 5806–5813 (1994)).

To evaluate the functional significance of the interaction of CD23 with CD11b or CD11c, we investigated whether CD23-CD11b/CD11c interaction could trigger monocytes to release proinflammatory mediators such as nitric oxide, $H_2O_2$ and cytokines. Triggering of adherence-activated normal monocytes using recombinant soluble CD23, anti-CD11b or anti-CD11c antibodies increased the generation of $NO_2$ indicating the activation of the NO pathway (Moncada, S., Palmer, R. M. J. & Higgs, E. A. *Pharmacol. Rev.* 43, 109–144 (1991)). The effect of CD23 on nitrite production was inhibited by Fab fragments of anti-CD23 monoclonal antibodies and by nitroarginine, a specific inhibitor of the NO synthase pathway (Example 9, FIG. 9a). The oxidative burst was also shown to be regulated through CD11b and CD11c since recombinant soluble CD23, anti-CD11b and anti-CD11c monoclonal antibodies all caused oxidation of hydroethidine to ethidium bromide in monocytes (Example 9, FIG. 9b). This confirms and extends the finding that anti-CD11b monoclonal antibodies induce an oxidative burst in monocytes (Trezzini, C., Schüepp, B., Maly, F. E. & Jungi, T. W. Brit. J. Haematol. 77, 16–24 (1991)). CD23 binding to CD11b and CD11c was associated with an early specific $Ca^{2+}$ flux in blood monocytes (not shown).

Since activated macrophages are an important source of proinflammatory cytokines, we evaluated the effect of recombinant soluble CD23 and of anti-CD11b and anti-CD11c monoclonal antibodies on the production of such cytokines by monocytes. Recombinant soluble CD23, anti-CD11b and anti-CD11c monoclonal antibodies were potent stimulators of IL-1, IL-6 and TNFα. Again, the specificity of this induction was demonstrated by using Fab fragments of anti-CD11b, anti-CD11c and anti-CD23 monoclonal antibodies (Example 10, FIG. 10). Interestingly, IL-1 and TNFα were potent inducers of CD23-liposome binding to monocytes (not shown), suggesting a potential cytokine autocrine loop through CD11b and CD11c stimulation and regulation.

Figure 5A:
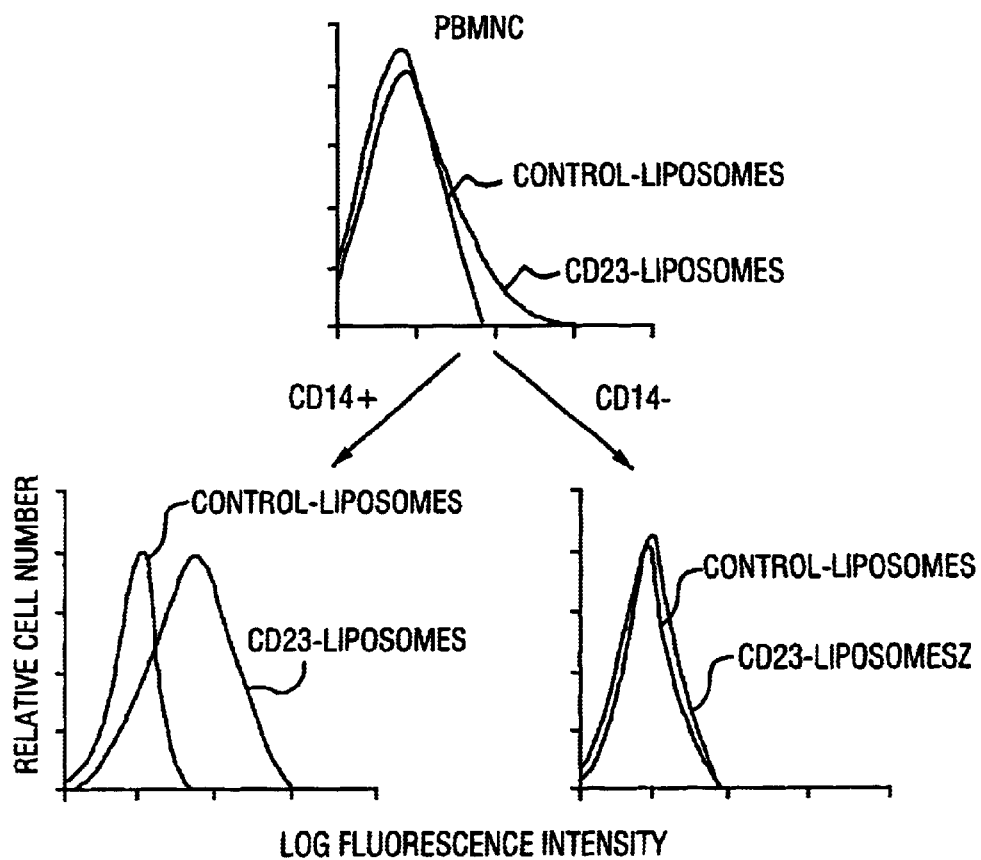
FIG. 5a illustrates CD23-liposomes binding to CD14 positive blood mononuclear cells.

Example 5 a) CD23-liposomes Bind to CD14Positive Blood Mononuclear Cells (See FIG. 5a)

Figure 5B:
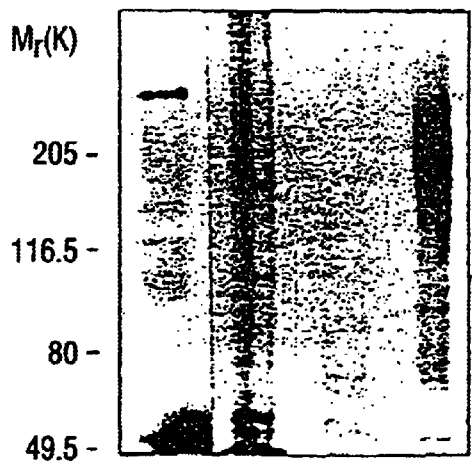
FIG. 5b illustrates various CD23 affinity purified proteins on SDS-PAGE gels.

Blood mononuclear cells were stained with anti-CD14 monoclonal antibody (Becton Dickinson, Erembodegem, Belgium) followed by sheep FITC-conjugated F(ab')$_2$ antibodies to mouse IgG and IgM (Bioart, Meudon, France), both diluted in PBS, 0.5% BSA and 0.05% sodium azide prior to FACS-sorting (FACStar Plus, Becton Dickinson) into CD14-positive and CD14-negative cell populations. Separated cells were then stained with CD23-liposomes or control (glycophorin A-liposomes diluted in 0.5% BSA, 0.1% sodium azide, 2 mM CaCl$_2$, 140 mM NaCl, 20 mM Hepes, pH 7 and incubated for 2 h at 4° C. (Pochon, S. et al., J. Exp. Med. 176 389–398 (1992)). After washes, cells (5,000 events/condition) were analysed by FACS.

b) Apparent Molecular Weight of CD23-affinity Purified Blood Monocyte Proteins and Immunoreactivity with an Anti-CD11c Monoclonal Antibody (See FIG. 5b)

Lysates of blood monocytes were affinity purified on a CD23-column, eluted proteins separated on SDS-PAGE gel and transferred onto nitrocellulose. Mr markers are shown on the left. The gel was silver stained (left lane). Filters were incubated with either an isotype matched antibody (middle lane) or with an anti-CD11c monoclonal antibody (BU-15, right lane), then with horseradish peroxidase-conjugated goat anti-mouse antibody (Kpl; Gaithersburg, Md.).

Example 6

Figure 6:
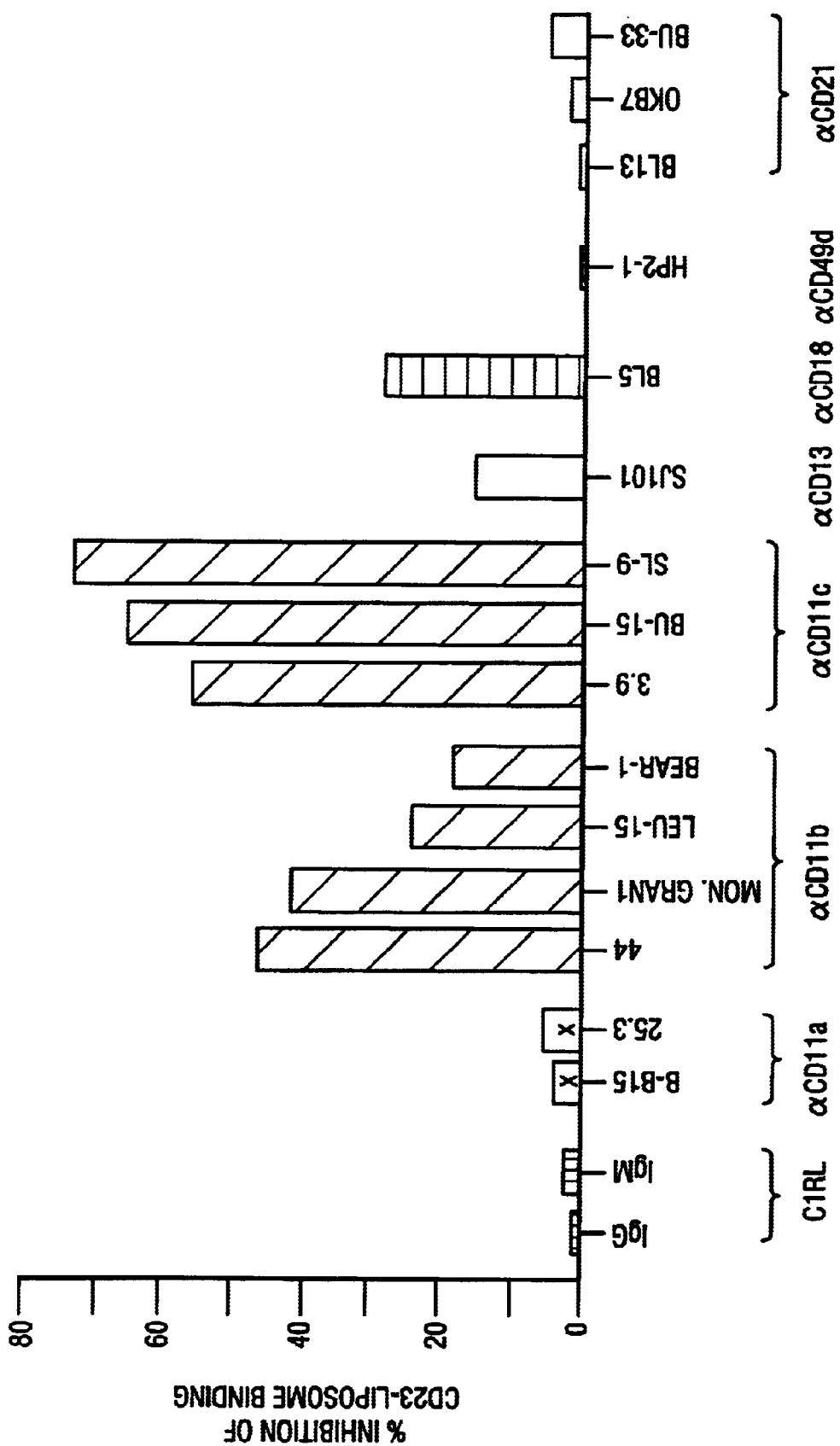
FIG. 6 illustrates the percentage inhibition of CD23-liposomes binding to activated blood monocytes obtained using certain monoclonal antibodies.

Anti-CD11b and Anti-CD11c Monoclonal Antibodies Decrease CD23-liposome Binding to Activated Blood Monocytes (See FIG. 6)

Monocytes were enriched from mononuclear cells by Ficoll and overnight adherence to plastic in RPMI 1640 (Seromed, Berlin, Germany) supplemented with 2 mM glutamine and 10% heat-inactivated FCS (Flow Laboratories, Irvine, Scotland). Activated monocytes were then incubated with CD23-liposomes in the presence of different monoclonal antibodies (αCD) or isotype-matched controls (CTRL) (Becton Dickinson), all tested at 10 μg/ml. Anti-CD11a monoclonal antibodies 25.3 and B-B15 were obtained from Immunotech (Luminy, France) and Serotec (Oxford, UK), respectively. Anti-CD11b monoclonal antibody 44 was from Serotec, mon.gran 1 was from Janssen (Beerse, Belgium), Leu-15 was from Becton Dickinson (Erembodegem, Belgium) and (Bear-1) was from Sera-Lab Ltd (Sussex, GB). Anti-CD11c monoclonal antibody 3.9 was from Serotec, SL9 was from Sera-Lab and BU-15 was from The Binding Site (Birmingham, UK). Anti-CD13 (SJ1D1), anti-CD18 (BL5), anti-CD23 (mAb25) and anti-CD49d (HP2.1) monoclonal antibodies were from Immunotech. Anti-CD21 monoclonal antibody BL13 was from Immunotech OKB7 from Ortho and BU-33 was obtained from Dr. MacLennan (Birmingham University, UK), HB-5 from ATCC, OKB7 from Ortho Diagnostics System Inc (Raritan, N.J.). Anti-CD14, anti-CD3, anti-CD16 and anti-CD20 monoclonal antibodies were from Becton-Dickinson Cells were analysed by FACS and mean fluorescence intensity (MFI) measured. Data of a representative experiment are presented. MFI of cells stained with control-liposomes was 6.5 and with CD23-liposomes was 84.5. Percentage inhibition using arithmetic linear MFI values is calculated according to the following formula:

$$\% \ inhibition = MFI \frac{[(CD23\text{-}lipo)] - [(CD23\text{-}lipo) + Mab]}{(CD23\text{-}lipo)} \times 100$$

Example 7

Figure 7:
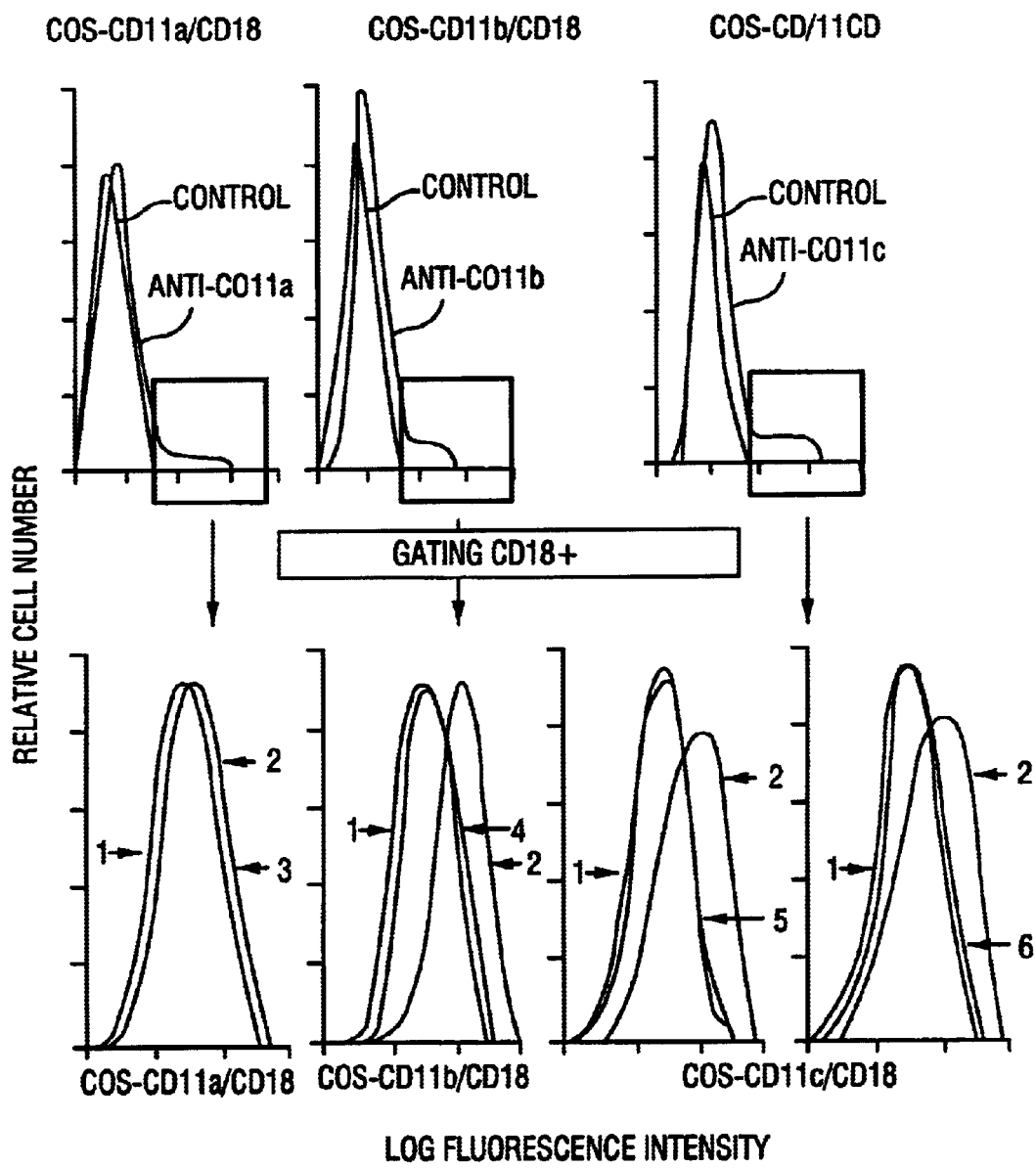
FIG. 7 illustrates the binding CD23 liposomes to various transfected cells.

CD23-liposomes Bind to α Chains of CD11b/CD18 and CD11c/CD18 on Recombinant Transfectants (See FIG. 7)

cDNAs coding for CD11a (Corbi, A. L., Miller, L. J., O'Connor, K., Larson, R. S. & Springer, T. A EMBO J. 6, 4023–4028 (1987)) was recloned in pCDNA1 (Invitrogen, San Diego, Calif.). cDNA for CD11b (Corbi, A. L., Kishimoto, T. K., Miller, L. J. & Springer, T. A. J. Biol. Chem. 263, 12403–12411 (1988)) and CD18 (Kishimoto, T. K., O'Connor, K., Lee, A., Roberts, T. M. & Springer, T. A. Cell 48, 681–690 (1987)) were recloned in pCDM8 (Seed, B., Nature 329 840–842 (1987)). 20 μg aliquots of DNA were transfected in COS-7 cells (ATCC) by electroporation (260 V, 960 μFD) using a Gene Pulser device (Bio-Rad, Richmond, Calif.) and 0.4 cm cuvettes in 20 mM Hepes pH 7.4, 150 mM NaCl. Co-transfections of CD11a, b or c with CD18 were performed in order to get expression of the β2 integrins at the cell surface. Controls were done with single chain transfections. 48 h after transfection, COS cells were stained with anti-CD11a, anti-CD11b and anti-CD11c monoclonal antibodies or isotype-matched monoclonal antibodies (control) followed by FITC-labelled sheep anti-mouse antibody. Between 10 to 15% of the cells were shown to express CD11a, b, c or CD18 by staining with the respective monoclonal antibodies. Prior to staining with CD23-liposomes, CD18-positive transfected COS cells were then FACS-sorted in order to increase the percentage of cells expressing α 2 integrins. CD11 a/CD18, CD11b/CD18 and CD11c/CD18 transfectants were then incubated with CD23-liposomes (trace 2) or control (glycophorin A)-liposomes (trace 1). The specificity of CD23 interaction with CD11b and CD11c was demonstrated by inhibition of CD23-liposome binding to CD11b/CD18 and CD11c/CD18 transfectants using anti-CD11b (trace 4), anti-CD23 (trace 5) and anti-CD11c (trace 6) monoclonal antibodies, respectively. No binding of CD23-liposomes was observed on CD11a/CD18 transfectants and no effect of anti-CD11a monoclonal antibody was found (trace 3).

Example 8
Structural Characterisation of CD23-CD11b, CD11c Interaction (See FIG. 8)
(a) Involvement of sugars and divalent cations Purified activated blood monocytes were treated or not with tunicamycin (10 μg/ml) for 48 h or with neuraminidase (0.1 U/ml; both from Boehringer Mannheim, Mannhein, Germany) for 45 min. Cells were then incubated with CD23-liposomes or control-liposomes in the absence or presence of EDTA (5 mM; top left panel), $Ca^{2+}$ or $Mn^{2+}$ (1 to 10 mM; top right panel).

(b) Factor X does inhibit CD23 binding to monocytes

Purified activated blood monocytes were incubated with CD23-liposomes in absence or presence of factor X (0.1 to 10 U/ml; Sigma) (bottom left panel), fibrinogen (50 μg/ml; Sigma), purified recombinant ICAM-1 (produced in our laboratory), LPS (1 μg/ml; Sigma), human serum opsonised-zymosan (1 mg/ml; Sigma), IgE (50 μg/ml; The Binding Site, Birmingham) or polyclonal antibody to RGD peptide (1/500. ATCC) (bottom right panel). Cells were analysed by FACS and MFI measured. Percentage inhibition was calculated as for Example 6.

Example 9
Recombinant CD23 by Binding to CD11b and CD11c Specifically Increases a. the Nitrite Product and b. the Oxidative Burst by Monocytes Monocytes were incubated a, for 4 days at 37° C. or b, overnight in the absence of presence of recombinant soluble CD23 (Graber P. et al., *J. Immunol. Methods* 149 215–226 (1992)) (50 ng/ml), anti-CD11a (clone 25.3), anti-CD11b (clone 44), anti-CD11c (clone BU-15) monoclonal antibodies (all at 10 μg/ml).

Figure 9A:
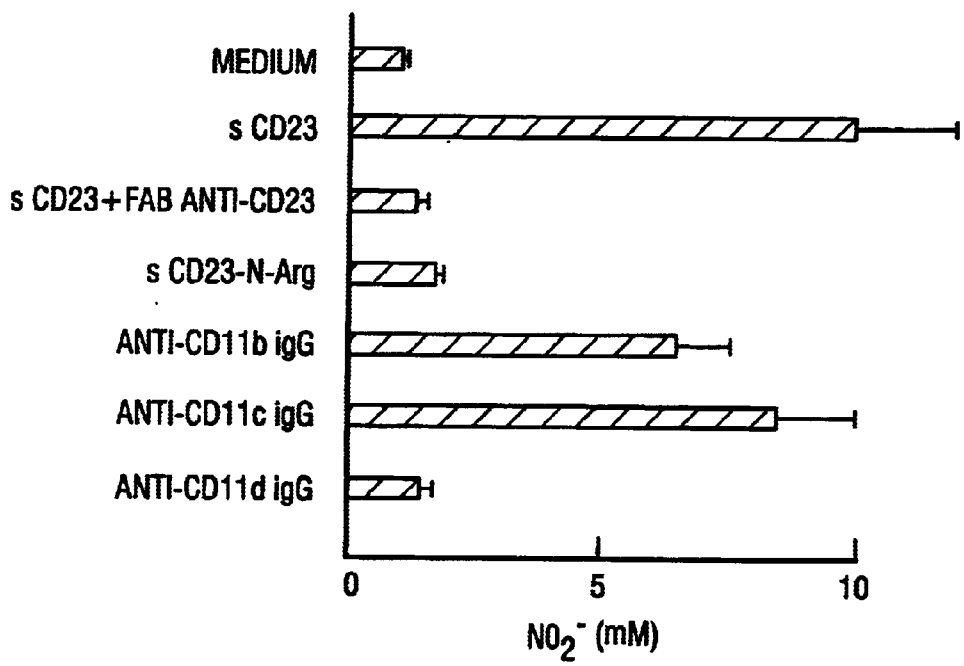
FIGS. 9A and 9B illustrate the effects on nitrite production and oxidative burst in monocytes caused by CD23 binding to CD11b and CD11c.
Figure 9B:
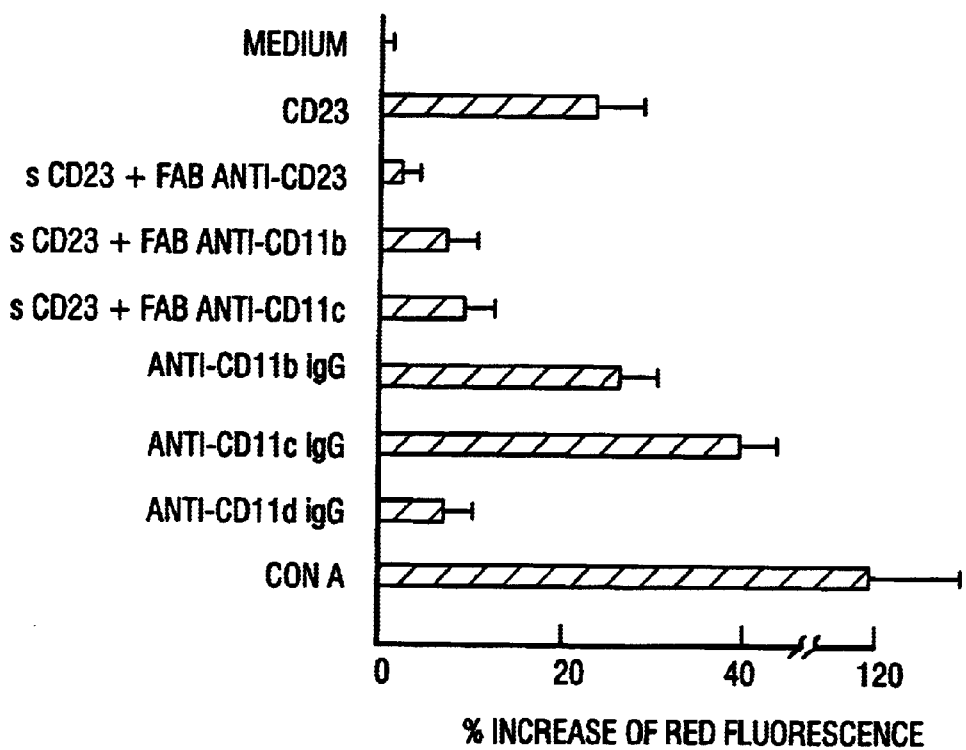

To assess the amount of NO produced (which is shown in FIG. 9a), the culture supernatants were assayed for the stable end products of NO, $NO_2^-$ and $NO_3^-$ according to Green et al., *Annu. Rev. Immunol.* 2 199–218 (1984). The specificity of CD23-mediated increase of $NO_2^-$ production was demonstrated by inhibition of $NO_2^-$ production by Fab fragments of anti-CD23 monoclonal antibodies (mab25) (tested at 10 μg/ml) and by inhibition with nitroarginine (N-Arg at 1 mM) (Sigma).

Activated monocytes were incubated with hydroethidine (Molecular probes, Eugene, Oreg.) (0.3 μg/ml) for 30 min at 37° C. (Rothe G. et al., *J. Leukoc. Biol.* 47 440–448 (1990)) and analysed by FACS. Percentage increase in red fluorescence of stimulated monocytes is shown in comparison to untreated monocytes (See FIG. 9b). Monocytes which had undergone an oxidative burst shown an increase of red fluorescence signals compared to untreated monocytes reflecting oxidation of hydroethidine to ethidium bromide (Lacal P. M. et al., *Biochem. J.* 268 707–712 (1990)). MFI values of monocytes alone were 159+/-10. Mean+/-SD values of 6 experiments are presented. Con A, which is known to induce a respiratory burst in monocytes, was used as a positive control. The specificity of the CD23 interaction with CD11b and CD11c was demonstrated by inhibition of CD23-mediated increase of $H_2O_2$ production by Fab fragments of anti-CD11b (clone 44), anti-CD11c (clone BU-15) and anti-CD23 (mAb25) monoclonal antibodies (tested at 10 μg/ml).

Figure 10:
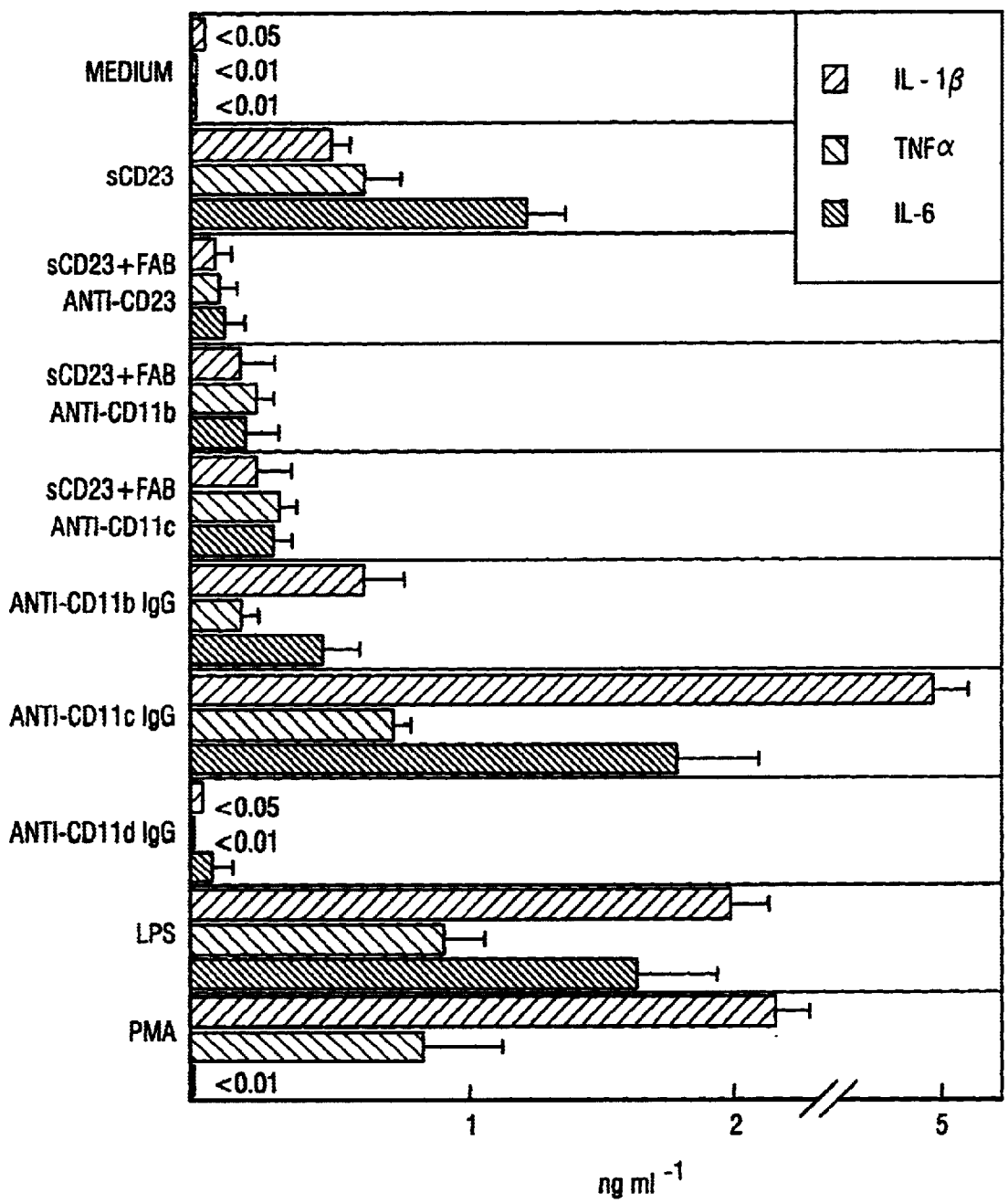
FIG. 10 illustrates that the binding of recombinant CD23 to CD11b and CD11c specifically increases cytokine production by monocytes.

Example 10
Binding of Recombinant CD23 to CD11b and CD11c Specifically Increases Cytokine Production by Monocytes (See FIG. 10)

Monocytes were incubated overnight at 37° C. in the absence or presence of recombinant soluble CD23 (Graber P. et al., *J. Immunol Methods* 149 215–226 (1992)) (50 ng/ml), anti-CD11a (clone 25.3), anti-CD11b (clone 44), anti-CD11c (clone BU-15), anti-CD23 (mAb 25—this antibody is available from Immunotech. It is discussed in published European Patent Application EP-A-0269728) monoclonal antibodies, Con A (Sigma) (all at 10 μg/ml), LPS (1 ng/ml) (Sigma) or PMA (5 ng/ml) (Calbiochem, La Jolla, Calif.). Cytokines were measured in the culture supernatant by specific ELISA The ELISA's limit of sensitivity is 0.05 ng/ml for IL-1β (Ferrua et al., *J. Immunol. Methods* 114 41–48 (1988)) 0.01 ng/ml for TNFα (Medgenix Biotechnie, Rungis, F) and <0.01 ng/ml for IL-6 (Manie et al., *Eur. Cytokine Netw.* 4 51–56 (1993)). The specificity of CD23 interaction with CD11b and CD11c was demonstrated by inhibition of CD23mediated increase of cytokine production by Fab fragments of anti-CD11b (clone 4), anti-CD11c (clone BU-15) and anti-CD23 (mAb25) monoclonal antibodies (tested at 10 μg/ml). Mean+/--SD values of 4 experiments are presented.

Example 11

Monoclonal antibodies to recombinant *E. coli* derived soluble human CD23 (25 kD, amino acids 150–321) were raised in mice, by standard procedures except using lymph nodes not spleen cells. These blocked the activities of human CD23 in vitro.

Example 12
Ulcerative Colitis 3 tamarin monkeys were dosed with anti-CD23 Mab without adverse effects, resulting in an improvement in subjective faecal score.

The dosage was 1 mg every 4 days by intramuscular injection.

Example 13

No toxic effects were observed in any tests reported here.
What is claimed is:

1. A method of treating an autoimmune disorder comprising administering to a patient in need of such treatment an amount of an agent that binds CD23, and thereby blocks the interaction of CD23 with a ligand to which CD23 binds in vivo, sufficient to effect said treatment.

2. The method according to claim 1 wherein said agent is an antibody.

3. The method according to claim 1 wherein said agent comprises a F(ab')$_2$, Fab, Fv or ScFv fragment of an antibody that binds CD23, or mimetic of said fragment.

4. The method according to claim 3 wherein said agent comprises a F(ab')$_2$, Fab, Fv or ScFv fragment of an antibody that binds CD23.

5. The method according to claim 1 wherein said ligand is CD21, CD11b or CD11c.

6. The method according to claim 1 wherein said autoimmune disorder is rheumatoid arthritis.

7. The method according to claim 6 wherein said CD23 is cell-associated CD23.

8. The method according to claim wherein said autoimmune disorder is arthritis, lupus erythematosus, systemic lupus erythematosus, Mashimotos thyroiditis, multiple sclerosis, diabetes, uveitis, dermatitis, psoriarsis, urticaira, nephrotic syndrome, glomerulonephritis, inflammatory bowel disease, ulcerative colitis, Crohn's disease, Sjogren's syndrome, asthma, eczema, graft vs host disease or insulitis.

9. The method according to claim 2 wherein said antibody is a humanized or chimaerized antibody.

10. The method according to claim 9 herein said antibody is a chimaerized antibody.

11. The method according to claim 1 wherein said agent administered in combination with an immunosuppressive, tolerance inducing, anti-autoimmune or anti-inflammatory agent.

12. The method according to claim 1 wherein said agent is administered in combination with a CD4+ T cell inhibiting agent or a TNF antagonist.

13. The method according to claim 5 wherein said CD4+ T cell inhibiting agent is an anti-CD4 antibody.

* * * * *

UNITED STATES PATENT AND TRADEMARK OFFICE
CERTIFICATE OF CORRECTION

PATENT NO.   : 6,627,195 B1
DATED        : September 30, 2003
INVENTOR(S)  : Bonnefoy It is certified that error appears in the above-identified patent and that said Letters Patent is hereby corrected as shown below:

<u>Title page,</u>
Item [75], Inventor, change "Jean-Yuves Marcel Paul" to
-- Jean-Yuves M.P. Bonnefoy --.

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO.    : 6,627,195 B1
DATED         : September 30, 2003
INVENTOR(S)   : Bonnefoy It is certified that error appears in the above-identified patent and that said Letters Patent is hereby corrected as shown below:

<u>Title page,</u>
Item [75], Inventor, change "Jean-Yves Marcel Paul" to
-- Jean-Yves M.P. Bonnefoy --.

This certficate supersedes Certificate of Correction issued January 6, 2004.

Signed and Sealed this

Twenty-third Day of March, 2004

JON W. DUDAS
*Acting Director of the United States Patent and Trademark Office*